US012571789B1

(12) United States Patent
Rogers et al.

(10) Patent No.: US 12,571,789 B1
(45) Date of Patent: Mar. 10, 2026

(54) MICROBIAL SUBSURFACE SOIL SENSORS

(71) Applicants:Raytheon BBN Technologies, Corp., Cambridge, MA (US); Worcester Polytechnic Institute, Worcester, MA (US)

(72) Inventors: Miles Rogers, Watertown, MA (US); Allison Taggart, Portsmouth, RI (US); Eric Young, Northborough, MA (US); Natalie Farny, Natick, MA (US); Nilesh Sharma, Worcester, MA (US); Andrés Felipe Carrillo Rincón, Worcester, MA (US); Jaclyn Thompson, Worcester, MA (US)

(73) Assignees: RTX BBN TECHNOLOGIES, INC., Cambridge, MA (US); WORCESTER POLYTECHNIC INSTITUTE, Worcester, MA (US)

( * ) Notice: Subject to any disclaimer, the term of this patent is extended or adjusted under 35 U.S.C. 154(b) by 714 days.

(21) Appl. No.: 17/984,869

(22) Filed: Nov. 10, 2022

Related U.S. Application Data

(60) Provisional application No. 63/329,328, filed on Apr. 8, 2022.

(51) Int. Cl.
G01N 33/24 (2006.01)
(52) U.S. Cl.
CPC .................................... *G01N 33/24* (2013.01)

(58) Field of Classification Search
CPC ....................................................... G01N 33/24
See application file for complete search history.

(56) References Cited

U.S. PATENT DOCUMENTS

| | | | | |
|---|---|---|---|---|
| 2019/0107509 A1* | 4/2019 | Burge | ...................... | A01G 7/00 |
| 2023/0030639 A1* | 2/2023 | Reardon | .......... | G01N 33/56961 |
| 2023/0304959 A1* | 9/2023 | Miller | ............... | G01N 27/3335 |

* cited by examiner

*Primary Examiner* — Jennifer Wecker
(74) *Attorney, Agent, or Firm* — CANTOR COLBURN LLP

(57) ABSTRACT

Methods of detecting a target analyte in subsurface soil can providing a bacterial consortium embodying a genetic circuit. Such a consortium can include a sensor bacterium, a signal propagation bacterium, and a display bacterium, which are provided at a soil surface. The sensor bacterium and signal propagation can be allowed to migrate into subsurface soil below the soil surface. The sensor bacterium can be exposed to the target analyte in the subsurface soil. The sensor bacterium can produce a signal molecule in response to the presence of the target analyte. The signal propagation bacterium can amplify the signal molecule by producing additional signal molecules in response to the presence of the signal molecule. The display bacterium can produce an observable signal in response to presence of the signal molecule.

29 Claims, 15 Drawing Sheets

Specification includes a Sequence Listing.

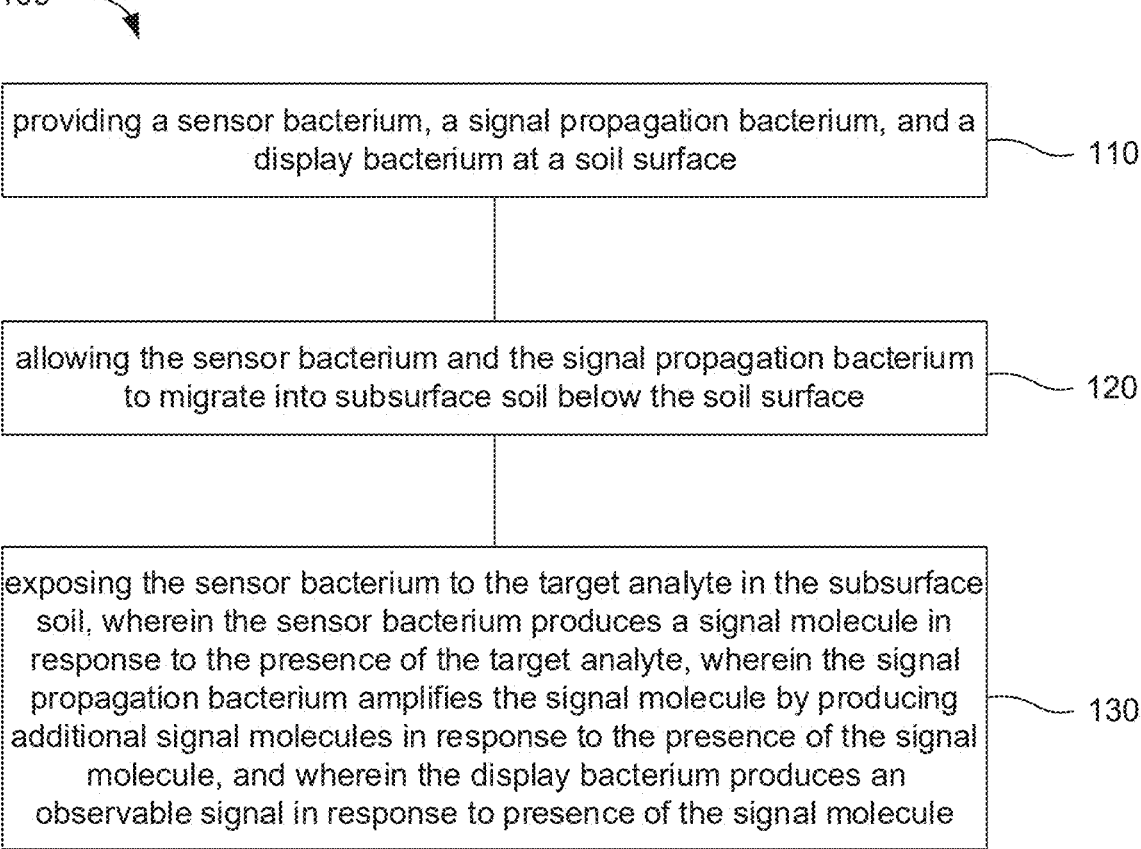

100 providing a sensor bacterium, a signal propagation bacterium, and a display bacterium at a soil surface — 110 allowing the sensor bacterium and the signal propagation bacterium to migrate into subsurface soil below the soil surface — 120 exposing the sensor bacterium to the target analyte in the subsurface soil, wherein the sensor bacterium produces a signal molecule in response to the presence of the target analyte, wherein the signal propagation bacterium amplifies the signal molecule by producing additional signal molecules in response to the presence of the signal molecule, and wherein the display bacterium produces an observable signal in response to presence of the signal molecule — 130

FIG. 1

MICROBIAL SUBSURFACE SOIL SENSORS

PRIORITY DATA

This application claims the benefit of U.S. Provisional Patent Application Ser. No. 63/329,328, filed Apr. 8, 2022 which is incorporated herein by reference in its entirety.

SEQUENCE LISTING

This application contains a sequence listing which is incorporated herein by reference in ST.26 XML format named 3721-170803US02_Sequence_Listing.xml, created Sep. 25, 2023, and is 13.2 KB in size. The sequences contained in the sequence listing are found throughout the originally filed application.

BACKGROUND

Biosensors include a variety of devices that combine a biological component with a transducer or detector element that can transform a signal from the biological component to a user-observable signal. Microbial biosensors are a specific class of biosensors, in which microbes are used as a component of the biosensor. Microbial biosensors can utilize a microbe, such as bacteria, that responds to a particular substance or other stimulus to be detected. Some bacteria have natural responses to certain substances, and these responses can be exploited in a biosensor by translating the response signal of the bacteria into a human-observable signal. Additionally, it is possible to genetically program bacteria to elicit certain observable behavior through mechanisms such as quorum sensing, and further, to utilize multiple types of bacteria, or multiple genetically engineered forms of a bacteria in order to create a circuit that performs logical functions.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 1 is a flowchart illustrating an example method of detecting a target analyte in subsurface soil, in accordance with an example of the present invention.

Figure 2:
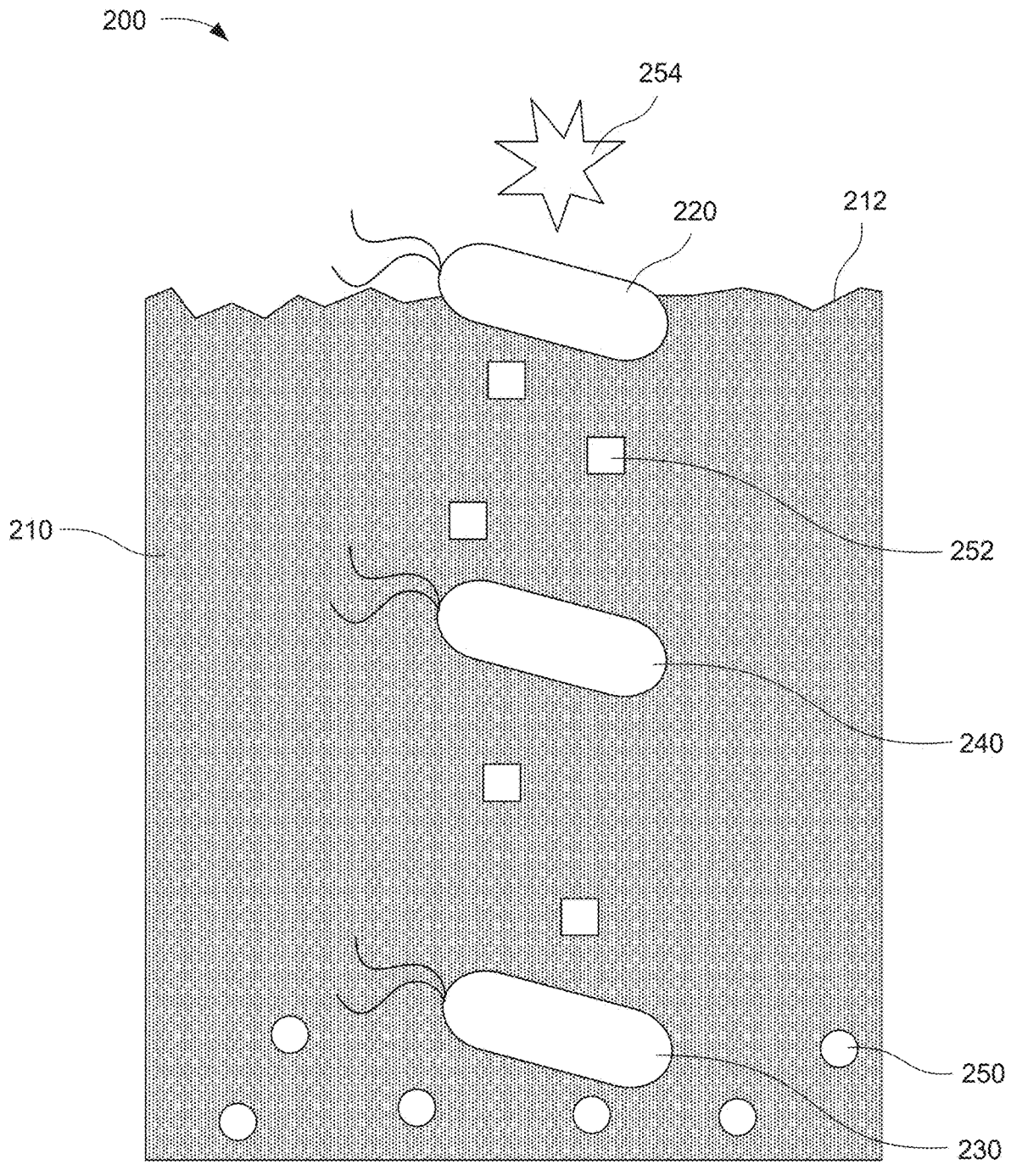
FIG. 2 is a schematic representation of an example microbial subsurface soil sensor in accordance with another example of the present invention.

Reference will now be made to the exemplary embodiments illustrated, and specific language will be used herein to describe the same. It will nevertheless be understood that no limitation of the scope of the invention is thereby intended.

DETAILED DESCRIPTION

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein, but are merely representative thereof.

Definitions

It should be noted that as used herein, the singular forms "a," "an," and, "the" include plural referents unless the context clearly dictates otherwise. Thus, for example, reference to "a bacterium" includes reference to one or more of such organisms, and reference to "analyte" includes reference to one or more of such analytes.

As used herein, the terms "formulation" and "composition" are used interchangeably and refer to a mixture of two or more compounds, elements, or molecules. In some aspects, the terms "formulation" and "composition" may be used to refer to a mixture of one or more active agents with a carrier or other material.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in the written description it is understood that direct support should be afforded also to "consisting essentially of" language as well as "consisting of" language as if stated explicitly and vice versa.

As is well known, the term "bacteria" is the plural form of the term "bacterium". Unless the specific context dictates otherwise, as used in the written description, bacterium and bacteria can be used interchangeably, and the recitation of one term provides express support for the other. Additionally, these terms can be used in connection with certain functional modifiers such as "sensor," "propagation," "display" and the like, and when so used refer to behaviors or actions taken by the bacteria. In some cases, the actions taken can be in response to stimuli received, such as environmental stimuli. Such actions or behavior can be either native to the particular bacterial species, or can be induced through genetic programming or engineering of the organism.

The term "sensor bacterium" refers to a bacterium that exhibits a specific behavior or activity (e.g. produces a signal molecule) when in the presence of, or in contact with a designated or specific analyte.

The term "propagation bacterium" refers to a bacterium that exhibits a specific behavior or activity such as produces a signal, in response to behavior or activity by a sensor bacterium.

The term "display bacterium" refers to a bacterium that behaves or acts in a way which displays or communicates a signal received from a propagation bacterium. For example, a display bacterium may be programmed to phosphoresce in response to the signal received from the propagation bacterium.

The term "signal molecule" refers to any chemical, agent, or substance produced by a bacterium that elicits a behavior or change in behavior of the bacterium, or of another bacterium. In one example, a signal molecule can be an autoinducer.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," "maximized," "minimized," and the like refer to a property of a device, component, composition, or activity that is measurably different from other devices, components, compositions or activities that are in a surrounding or adjacent area, that are similarly situated, that are in a single device or composition or in multiple comparable devices or compositions, that are in a group or class, that are in multiple groups or classes, or as compared to the known state of the art.

The term "coupled," as used herein, is defined as directly or indirectly connected in a chemical, mechanical, electrical or nonelectrical manner. Objects described herein as being "adjacent to" each other may be in physical contact with each other, in close proximity to each other, or in the same general region or area as each other, as appropriate for the context in which the phrase is used. "Directly coupled" objects, structures, elements, or features are in contact with one another and may be attached. Further as used in this written description, it is to be understand that when using the term "coupled" support is also afforded for "directly coupled" and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Embodiments

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

The present disclosure describes methods of detecting target analytes in subsurface soil and surface-dispersible microbial sensors that can be used to detect target analytes in subsurface soil. The methods can utilize a microbial biosensor that can detect an analyte present below the surface of the soil. The microbial biosensor can also transmit a signal from the subsurface soil up to the surface, where the signal can be observed, for example by fluorescence output and detection.

Although a variety of microbial biosensors have been created for detecting various analytes, some of which might be on a soil surface, it has nevertheless been more difficult to detect the presence of analytes in soil below the surface. The methods and sensors described herein can be particularly useful for detecting analytes in subsurface soil without taking direct samples of the subsurface soil. In some examples, the methods described herein can be used without disturbing the soil (or other geologic formation) at all, or with only a small disturbance of taking a sample of top surface-level soil.

In some examples, the microbial biosensors can include a sensor bacterium, a signal propagation bacterium, and a display bacterium. An example method of detecting a target analyte in subsurface soil can include providing the sensor bacterium, signal propagation bacterium, and display bacterium at the soil surface. The sensor bacterium and the signal propagation bacterium can be allowed to migrate into the subsurface soil below the soil surface. The sensor bacterium can then be exposed to the target analyte in the subsurface soil. The sensor bacterium can produce a signal molecule in response to the presence of the target analyte. The signal propagation bacterium can amplify the signal molecule by producing additional signal molecules in response to the presence of the signal molecule. The display bacterium can produce an observable signal in response to the presence of the signal molecule.

FIG. 1 is a flowchart illustrating one specific example method 100 of detecting a target analyte in subsurface soil in accordance with the present disclosure. This method includes: providing a sensor bacterium, a signal propagation bacterium, and a display bacterium at a soil surface 110; allowing the sensor bacterium and the signal propagation bacterium to migrate into subsurface soil below the soil surface 120; and exposing the sensor bacterium to the target analyte in the subsurface soil, wherein the sensor bacterium produces a signal molecule in response to the presence of the target analyte, wherein the signal propagation bacterium amplifies the signal molecule by producing additional signal molecules in response to the presence of the signal molecule, and wherein the display bacterium produces an observable signal in response to presence of the signal molecule 130.

FIG. 2 is a schematic representation of a microbial subsurface soil sensor 200 in accordance with an example of the present disclosure. A cross-section of soil 210 is shown. A display bacterium 220 is located at the soil surface 212. A sensor bacterium 230 and a signal propagation bacterium 240 migrate into the subsurface soil below the soil surface. In this example, a target analyte 250 is present in the subsurface soil. The target analyte can be a chemical compound, but in this figure is represented by circles. The sensor bacterium can respond to the presence of the target analyte by producing a signal molecule 252, represented by squares in this figure. The signal propagating bacterium responds to the presence of the signal molecule by producing more signal molecules. This creates a feed-forward effect as the signal molecule causes more signal molecules to be produced. The signal molecules can continue to be detected by signal propagating bacteria up through the subsurface soil until the signal molecule reaches the soil surface. The display bacterium at the soil surface can respond to the presence of the signal molecule by producing an observable signal. In this figure, the observable signal can be fluorescence, represented by a star 254. The observable signal can be directly observable (e.g., by a human eye or camera, or other optical detector) or may be observable using a process such as flow cytometry. For example, a sample of the display bacteria at the soil surface can be taken and the fluorescence level of the display bacteria can be quantified using flow cytometry. Any detectible signal or change can be used, including visual signals, auditory signals, olfactory signals, changes in electrical conductivity, chemistry, bacterial growth and concentration, other organism growth or population changes, etc., including signals that are detected with instrumentation, such as IR, FTIR, or other spectroscopy or spectrophotometry or other instrumentation required to detect a target signal activity.

Some bacteria can migrate from the soil surface into the subsurface soil through motility of the individual bacteria, spreading of the bacteria through reproduction, or a combination thereof. Some bacteria can also be capable of propagating signal molecules through the soil as explained above without any additional help or pathways for propagating the signal. However, in some examples a filamentous fungus can be present with the bacteria. Fungal filaments can facilitate both the migration of bacteria into the soil and the transmission of signals through the soil. In some examples, the fungus can allow the bacteria to form a biofilm on surfaces of filaments of the fungus. Without being bound to a specific theory, it is believed that some filamentous fungi can form an aqueous film around filaments of the fungus, and bacteria can swim in this aqueous film. This can allow bacteria to migrate more quickly by using the filaments as "highways" through the soil. In further examples, the fungus can exchange nutrients and other chemical compounds with bacteria. This can allow signal molecules to be transferred between bacteria more quickly and over greater distances.

Figure 3:
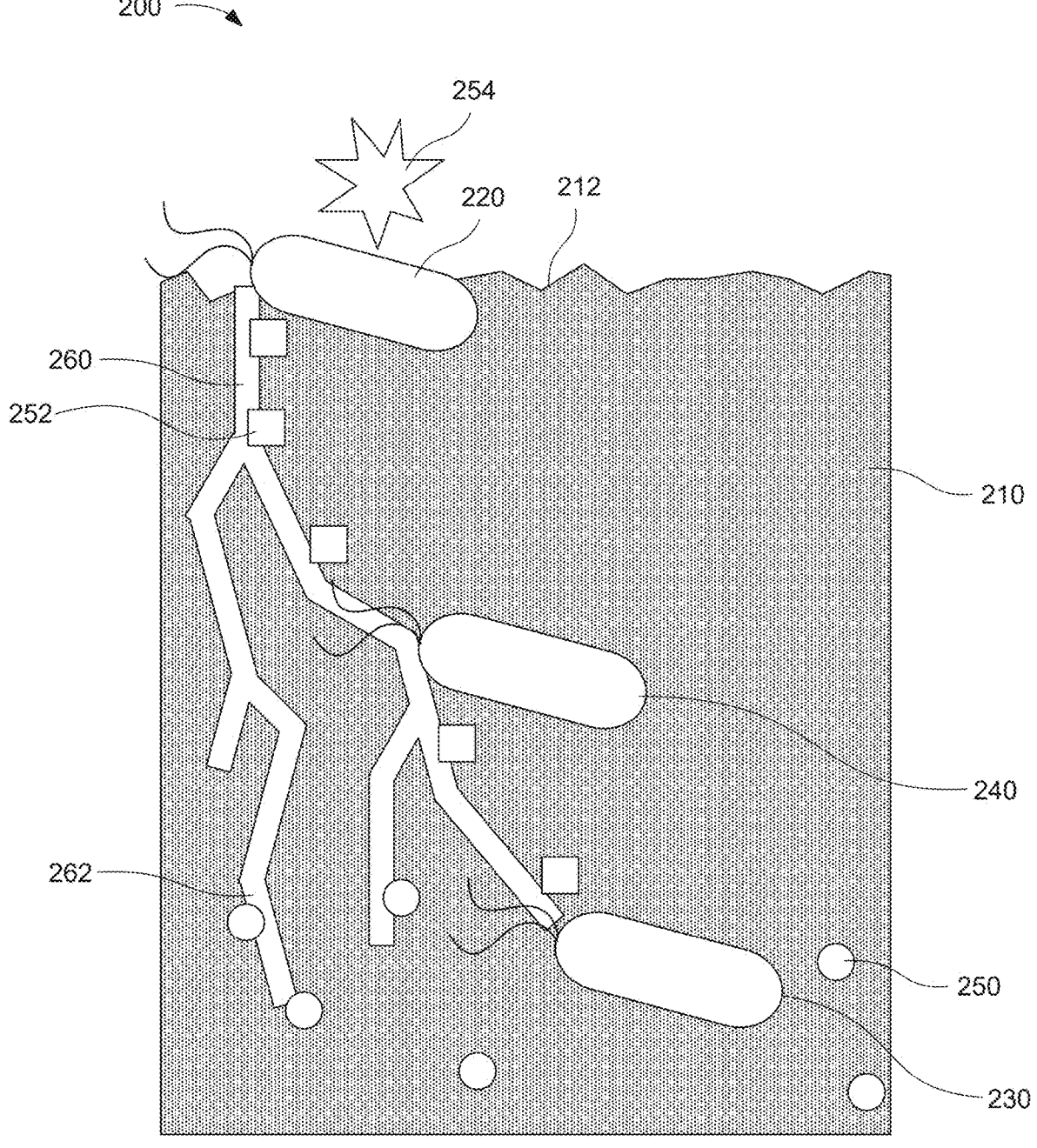
FIG. 3 is a schematic diagram of another example microbial subsurface soil sensor in accordance with an example of the present invention.

FIG. 3 is a schematic representation of another example microbial subsurface soil sensor 200. This example includes a fungus 260 having filaments (e.g. mycelia and/or hyphae) 262 in the subsurface soil. The sensor also includes a sensor bacterium 230, a signal propagation bacterium 240, and a display bacterium 220 as in the previous example. The sensor bacterium can respond to a target analyte 250 by producing a signal molecule 252. The signal propagation bacterium can propagate the signal by producing additional signal molecules in response to the presence of the signal molecule. The display bacterium can produce an observable signal 254 in response to the presence of the signal molecule. In this example, the bacteria can associate with the filaments of the fungus. The fungus can facilitate migration of the sensor bacterium, or the migration of the signal propagation bacterium, or the transfer of signal molecules between the bacteria, or a combination thereof. For example, the bacteria themselves can move along the filaments, and/or the target analyte and signal molecules can move along the filaments. Thus, the filaments can help the bacteria detect the target analyte and send the signal to the display bacteria at the soil surface.

Regarding the fungus that may be used with the bacteria in the sensors described herein, a variety of soil fungi can be used. Some specific examples of fungus that can be used include *Lyophyl atratum, Rhizopus oryzae, Fusarium* sp., *Fusarium oxysporum, Fusarium chlamydosporum, Fusarium equiseti, Fusarium nygamai, Chaetomium* sp., *Chaetomium globosum, Morchella crassipes, Trichoderma* sp., and combinations thereof. In further examples, the fungus can be a type of fungus that exchanges nutrients with the bacteria in the soil. Thus, nutrients and other compounds can be transferred from the bacteria to the fungus or from the fungus to the bacteria. In some examples, the target analyte and/or the signal molecule can be transferred to the fungus by the bacteria, or transferred to the bacteria by the fungus. In further examples, the target analyte and/or signal molecule can be transported by the filaments of the fungus through the soil. This can increase the speed of signal propagation compared to diffusion of the signal compound through the soil without the fungus.

The fungus can spread through the soil to a sufficient depth to facilitate detection of the target analyte in the subsurface soil. In some examples, the fungus can include filaments that reach a depth of at least 5 cm beneath the soil surface, or at least 8 cm beneath the soil surface, or at least 10 cm beneath the soil surface, or at least 20 cm beneath the soil surface, or at least 50 cm beneath the soil surface, or at least 100 cm beneath the soil surface, in some examples. It can also be useful to use a fungus that grows filaments quickly and spreads quickly through the soil. In some examples, the fungus can grow filaments spreading through the soil at a rate from about 0.5 mm/day to about 10 mm/day, or from about 1 mm/day to about 10 mm/day, or from about 2 mm/day to about 10 mm/day, or from about 5 mm/day to about 10 mm/day.

In further examples, the fungus can be capable of forming a biofilm comprising the sensor bacterium, the signal propagation bacterium, the display bacterium, or a combination thereof. The biofilm can include an aqueous layer that can allow bacteria to move more quickly than the bacteria can move through normal soil. The fungus and bacteria can be applied at the soil surface in some cases. The fungus can grow filaments downward into the soil and the filaments can provide a pathway for the bacteria to move beneath the soil more quickly.

Regarding the bacteria used in the microbial sensors, the sensors can utilize a sensor bacterium, a signal propagation bacterium, and a display bacterium. It is noted that the term "bacterium" can refer to a single bacterial cell, or multiple cells of a single bacterial strain, or multiple different bacterial strains or bacterial species. In more detail, the sensor bacterium can be a bacterium that is sensitive toward a target analyte such that the sensor bacterium produces a signal molecule when the target analyte is present. The signal propagation bacterium can be a bacterium that is sensitive toward the signal molecule. The response of the signal propagation bacterium can be to produce more of the signal compound when the signal compound is present. Thus, the signal propagation bacterium amplifies the signal originating from the sensor bacterium. The display bacterium can be a bacterium that is also sensitive toward the signal compound, but the response of the display bacterium can be to produce some sort of observable signal in response to the presence of the signal molecule.

Additionally, in some examples a single bacterial strain can perform multiple roles selected from sensing, signal propagation, and display. For example, one bacterial strain can be sensitive toward the signal molecule and the bacterium can have two responses that occur in the presence of the signal molecule. The first response can be the production of additional signal molecules. The second response can be an observable signal, such as fluorescence. Such a bacterial strain can be used as both the signal propagation bacterium and the display bacterium. In another example, one bacterial strain may be sensitive toward the target analyte and also sensitive toward the signal molecule. However, the response of the bacterium can be to produce signal molecules when either the target analyte or the signal molecule is present. This bacterial strain can be used as both the sensor bacterium and the signal propagation bacterium. In yet another example, one bacterial strain can perform all three roles. This bacterial strain can be sensitive to both the target analyte and the signal molecule. The bacterium can respond to the presence of the target analyte by producing the signal molecule. The bacterium can also respond to the presence of the signal molecule by producing additional signal molecules and by producing an observable signal such as fluorescence.

The target analyte can be any material that is desired to be detected, and for which a sensor bacterium can be found or engineered to respond to the presence of the target analyte. In some examples, it may be useful to use the microbial sensors described herein to detect explosive compounds. For example, trinitrotoluene and dinitrotoluene are chemical compounds that may be found in proximity to explosives. A microbial sensor that can detect such explosive compounds can be useful for safely locating landmines, munitions, and other explosives. In further examples, the microbial sensors can detect pollutants. Such sensor may be useful for determining extent of pollution from a particular pollution source, or for monitoring soil remediation of polluted soil. In other examples, the target analyte can be a nutrient, a sugar, a pharmaceutical, a quorum sensing molecule, a homoserine lactone, or a combination thereof.

The various bacteria used in the microbial sensors described herein can be naturally occurring bacteria, engineered bacteria, or a combination thereof. In some examples, the sensor bacterium or the signal propagation bacterium or the display bacterium can be naturally occurring bacteria. The naturally occurring bacteria can have a natural sensitivity and response to the target analyte and/or the signal molecule. However, in many examples the desired response can be induced in a bacterium by genetic modification. In one example, a sensor bacterium can be made by modifying the genes of a bacterium such that the bacterium produces a signal molecule in response to the presence of a target analyte. In another example, a signal propagation bacterium can be made by modifying the genes of a bacterium such that the bacterium produces signal molecules in response to the presence of the signal molecule. Similarly, a display bacterium can be made by modifying the genes of a bacterium such that the bacterium produces an observable signal, such as fluorescence, in response to the present of the signal molecule. In certain examples, the display bacteria can produce a fluorescent protein when the signal molecule is present.

The sensor bacterium, signal propagation bacterium, display bacterium, or a combination thereof can implement a quorum sensing genetic circuit in some examples. Quorum sensing can refer to regulation of gene expression in response to changes in population density of bacterial cells. In a quorum sensing genetic circuit, the bacteria can produce a quorum sensing molecule, which can be excreted outside the bacterial cells. In naturally-occurring quorum sensing, the quorum sensing molecules accumulate outside the cells. When the population density of cells reaches a certain threshold, the concentration of quorum sensing molecules outside the cells becomes large enough that it is unfavorable for more quorum sensing molecules to be transferred from the inside of the cells to the outside of the cells. The quorum sensing molecules then begin to build up inside the cells, and the increased concentration of the quorum sensing molecules can affect how genes are expressed in the cells. Often, this effect can include downregulation of the production of the quorum sensing molecules by the cells, but a variety of other effects can be triggered as well. Genetic modification can allow for this system to be "hijacked" and a variety of different genetic expressions can be linked to the increased concentration of quorum sensing molecules.

In certain examples, the signal molecules utilized in the sensors described herein can be a quorum sensing molecule. Examples of quorum sensing molecules can include homoserine lactones. Some specific examples include N-(3-oxododecanoyl)-L-homoserine lactone (abbreviated as 3O-C12-HSL) and N-(3-oxohexanoyl)-L-homoserine lactone (abbreviated as 3O-C6-HSL). Some naturally occurring bacteria include genes that are responsive to the concentration of quorum sensing molecules. Such bacteria can be used in the sensors described herein. In some examples, the bacteria can be engineered to have a different response caused by the presence of the quorum sensing molecules compared to un-engineered bacteria. In further examples, the genes that are responsive to the quorum sensing molecules can be added to another bacterium through genetic modification. As an example, 3O-C12-HSL is a quorum sensing molecule used in the LasR-LasI system of the bacterium *Pseudomonas aeruginosa*. LasR is a transcriptional activator that responds to the 3O-C12-HSL. The 3O-C12-HSL is a product of LasI synthase. A large number of genes in this bacterium are activated when a sufficient concentration of 3O-C12-HSL is present. As another example, the LuxR-LuxI system of the bacterium *Vibrio fischeri* involves genes encoding the signal synthase LuxI and the signal receptor LuxR. The LuxI protein synthesizes 3O-C6-HSL, and the LuxR receptor is activated by a sufficiently high concentration of 3O-C6-HSL. A variety of other quorum sensing molecules and systems exist in other organisms. In some examples, the genes responsive to a quorum sensing molecule (such as the receptors LuxR and LasR) and the genes responsible for synthesizing the quorum sensing molecule (such as LuxI and LasI) can be inserted into other bacteria through genetic modification. These particular quorum sensing systems are used in gram-negative bacteria. Therefore, in some examples the bacteria of the sensors described herein can be gram-negative bacteria.

As mentioned above, quorum sensing molecules can be used as the signal molecule in the sensors described herein. In some examples, the same quorum sensing molecule can also be the target analyte. Thus, the sensor bacterium and the signal propagation bacterium can both be sensitive toward the target quorum sensing molecule, and can produce additional quorum sensing molecules in response to the presence of the quorum sensing molecule. In further examples, the sensor bacterium, signal propagation bacterium, and display bacterium can all be a single bacterial strain. These bacteria can also produce an observable signal in response to the presence of the target quorum sensing molecule. In certain examples, the observable signal can be the production of a fluorescent protein.

Figure 4:
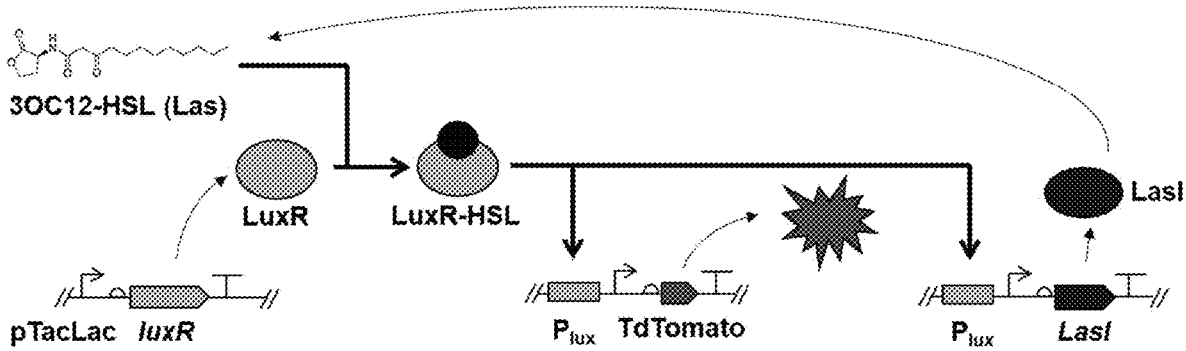
FIGS. 4-7 are example genetic circuits that can be implemented in bacteria in accordance with examples of the present invention.

FIG. 4 is a genetic circuit diagram illustrating an example quorum sensing genetic circuit that can be implemented by a bacterium in the sensors described herein. In this genetic circuit, 3O-C12-HSL is an input that is also produced by the LasI protein within the genetic circuit. The protein LuxR is produced from the LuxR gene, and the LuxR protein and 3O-C12-HSL together activate the promoters Plux. In this genetic circuit, the Plux promoter is included on a gene for producing a red fluorescent protein, TdTomato, and on a gene for producing the LasI protein. This bacterium can act as a sensor bacterium for sensing 3O-C12-HSL as the target analyte, and as a signal propagation bacterium by producing additional 3O-C12-HSL, and as a display bacterium by producing the red fluorescent protein.

Figure 5:
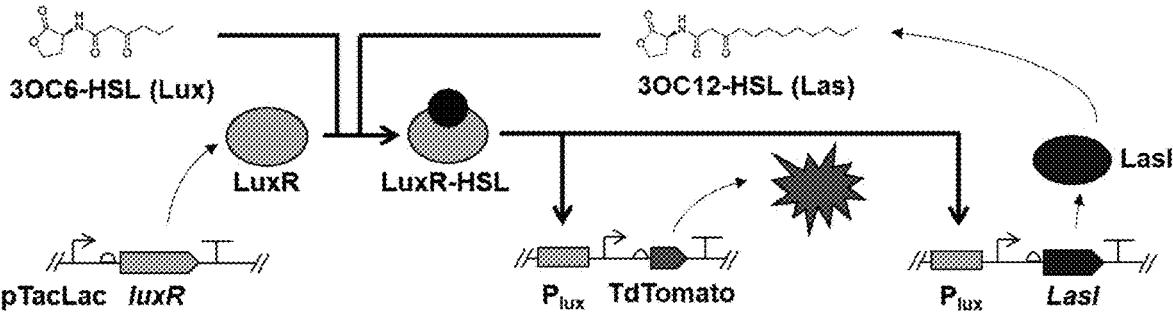

FIG. 5 is another genetic circuit diagram illustrating another example quorum sensing genetic circuit. This example includes the same genes as in the previous example, except the target analyte that is input in this example is 3O-C6-HSL. The 3O-C6-HSL can also work with the LuxR protein similar to the 3O-C12-HSL, so the when 3O-C6-HSL is present the Plux promoters can be activated. The bacterium can then produce 3O-C12-HSL, which can at as a signal molecule. Thus, the bacterium can also act as a sensor bacterium for detecting 3O-C6-HSL as the target analyte, and as a signal propagation bacterium, and as a display bacterium.

Figure 6:
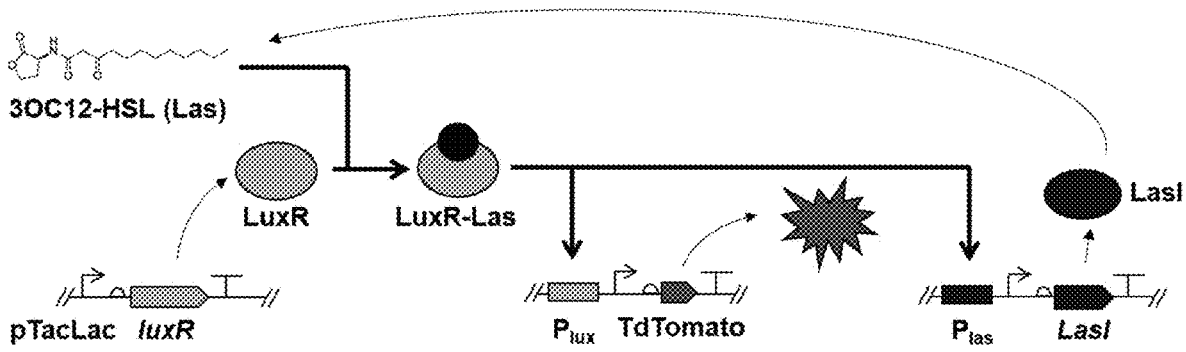

FIG. 6 is another genetic circuit diagram illustrating another example quorum sensing genetic circuit. The genes in this example are the same as in the previous examples except that a different promoter, Plas, is used on the gene for producing the LasI protein. In this circuit, 3O-C12-HSL is input as the target analyte, and the 3O-C12-HSL together with the protein LuxR can activate the promoter Plux on the TdTomato gene to produce the red fluorescent protein, and can also activate the Plas promoter on the gene to produce the LasI protein. Thus, this bacterium can also work as a sensor bacterium, signal propagation bacterium, and display bacterium.

Figure 7:
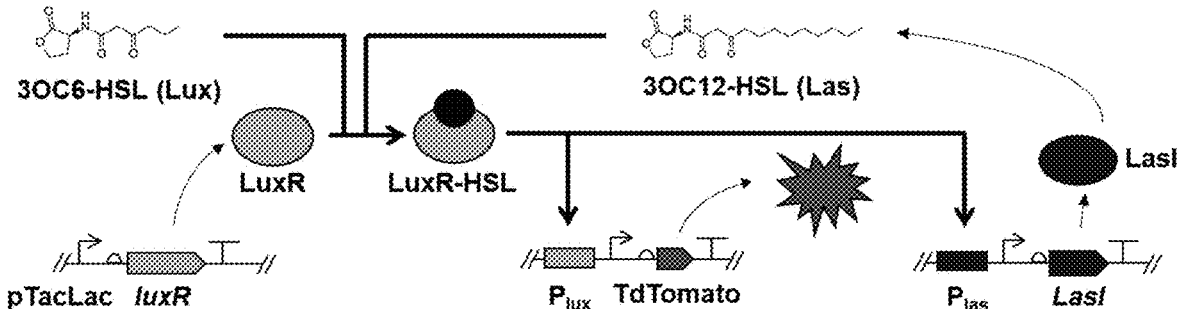

FIG. 7 is yet another genetic circuit diagram illustrating another example quorum sensing genetic circuit. This example has the same genes as in FIG. 6, but the target analyte is 3O-C6-HSL. The 3O-C6-HSL can work similarly to the 3O-C12-HSL and both can work together with the LuxR protein to activate the Plux and Plas promoters. Thus, this bacterium can act as a sensor bacterium to detect 3O-C6-HSL. The bacterium can also produce 3O-C12-HSL

11 as a signal molecule and the bacterium can produce red fluorescent protein as an observable display signal.

Although these examples use a quorum sensing molecule as the target analyte to be detected, these genetic circuits can be modified to detect a variety of other target analytes. For example, a promoter can be linked to a gene for producing a signal molecule, where the promoter is activated at a sufficient concentration of whatever target analyte is desired to be detected. Thus, the presence of the target analyte can trigger the production of a signal molecule and the bacterium can also include a gene for producing additional signal molecules with a promoter that is activated by the presence of the signal molecule, as in the examples of FIGS. 4-7. The bacterium can also include a gene for producing a fluorescent protein that is activated by the presence of the signal molecule as in these examples.

The present systems and methods can also be used in conjunction with known microbial sensors. In particular, known biosensors that allow a bacterium to detect a particular target analyte can be implemented in a sensor bacterium as described herein through proper genetic modification. The sensor bacterium can then be used together with a signal propagation bacterium and a display bacterium as described herein to form a subsurface soil sensor. As explained above, in some examples one or more of the sensor bacterium, signal propagation bacterium, and display bacterium can be a single bacterial strain that performs multiple of these functions. In some examples, a known biosensor can be implemented in a bacterium by genetic modification, and the same bacterium can also be modified to act as a signal propagation bacterium and/or a display bacterium.

Because the sensors described herein are for use in subsurface soil, it can be useful to implement the genetic circuits described herein in bacteria that are well-adapted for living in soil. Additionally, the bacteria can be capable of migrating from the surface of the soil into the subsurface soil. In certain examples, the bacteria can be compatible with a filamentous fungus so that the filamentous fungus can facilitate the migration of the bacteria through the soil, and/or the bacteria can transfer nutrients and other compounds to and from the fungus. Some examples of specific bacterial species that can be used in the sensor include: *Pseudomonas putida*, *Pseudomonas frederiksbergensis*, *Escherichia coli*, *Variovorax soli*, *Olivibacter soli*, *Acinetobacter calcoaceticus*, *Stenotrophomonas maltophilia*, *Stemotrophomonas rhizophila*, *Stenotrophomonas humi*, *Achromobacter spanius*, *Achromobacter mucicolens*, *Ochrobactrum* sp., *Ochrobactrum pecoris*, and others.

A chemoattractant can also be used with the bacteria of the sensors. In some examples, a chemoattractant can be applied to the soil surface to attract bacteria to toward the surface. This can encourage the signal propagation from the sensor bacterium in the subsurface soil to the display bacterium at the surface, and in some cases this can provide a stronger display signal when the target analyte has been detected. In certain examples, the chemoattractant can include salicylic acid.

The methods of detecting a target analyte in subsurface soil as described herein can include providing the sensor bacterium, signal propagation bacterium, and display bacterium at the soil surface. In some examples, the bacteria can be provided by spreading the bacteria on the soil surface without disturbing the soil surface, or by mixing the bacteria into the surface soil, or by inserting plugs containing the bacteria into the soil. The bacteria can formulated together as a surface-dispersible microbial sensor, which can be dispersed at the soil surface in any of these ways. If a fungus is used in the sensor, then the fungus can be provided in the same way. In various examples, a surface-dispersible microbial sensor can include the bacteria and fungus in a liquid media that can be sprayed or otherwise dispersed on the soil surface. Alternatively, the bacteria and fungus can be infused in a particulate material such as soil, and the particulate material can be dispersed on the soil surface.

EXAMPLES

Multiple examples of microbial sensors for detecting a target analyte in subsurface soil were made and tested using the following procedures.

Micro-Organism and Culture Condition 5 fungal strains: *Laccaria proxima* (CBS-378.74), *Lyophylum atratum* (CBS-144462), *Morchella crassipes* (CBS-274.88), *Rhizopus oryzae* (ATCC-10404) and *Neurospora crassa* (ATCC-44320) were procured from a culture collection center. Bacterial strains *Pseudomonas putida* KT2440 and AG4774 were gifted from Professor Adam Guss' Lab, Oak Ridge National Laboratory, Oak Ridge, TN, United States. Fungal strains were grown on oat flakes agar (OFA) and potato dextrose agar (PDA) and soil and incubated at 25° C. *P. putida* KT2440 and AG4774 were grown on luria broth (LB) (BP1426, Fisher scientific, USA), M9 media, and soil extract and incubated at 30° C.

Growth Media Composition and Preparation

OFA was composed of oat flakes (30 g/L), and agar (15 g/L). OFA was prepared by boiling oat flake at 60° C. for 15 min followed by oat flake extract was mixed in 1 L deionized water. Further agar was added and autoclaved. Garden soil was procured from Home Depot and autoclaved for 30 min at 121° C. *P. putida* cells were also grown on M9 media with composition (g/l): Di-Sodium hydrogen phosphate, 3; Potassium dihydrogen phosphate, 1.5; Sodium chloride, 0.25; Ammonium chloride, 0.5; and Glucose, 20; together with 2 mM Magnesium sulfate and 100 UM Calcium chloride. Soil extract was prepared by boiling soil at 80° C. for 30 min followed by sequentially filtering with water sieve, 0.5 μm filter paper, and 0.2 μm filter.

Soil Plate and Column Preparation

A radial growth study of the fungal strain was performed to test the horizontal radial growth and vertical radial growth of the fungal strains. Soil plate were prepared using 100 mm petri dishes filled with 10 gm sterilized soil. Soil columns were also prepared on different scales including 80 mm, 250 mm and 500 mm. For the small scale study, falcon tubes were used for the 80 mm column and sampling ports were made at distances of 20 mm and 45 mm from the top. The tubes were filled with 10 gm of sterilized soil. Medium (250 mm) and large (500 mm) size soil columns were made with PVC pipes. Medium size soil columns had three sample ports at 0, 75 and 150 mm distances from the top. Large columns also had three sampling port at 0, 250 and 500 mm distances from the top.

Fungal Growth

Figure 8:
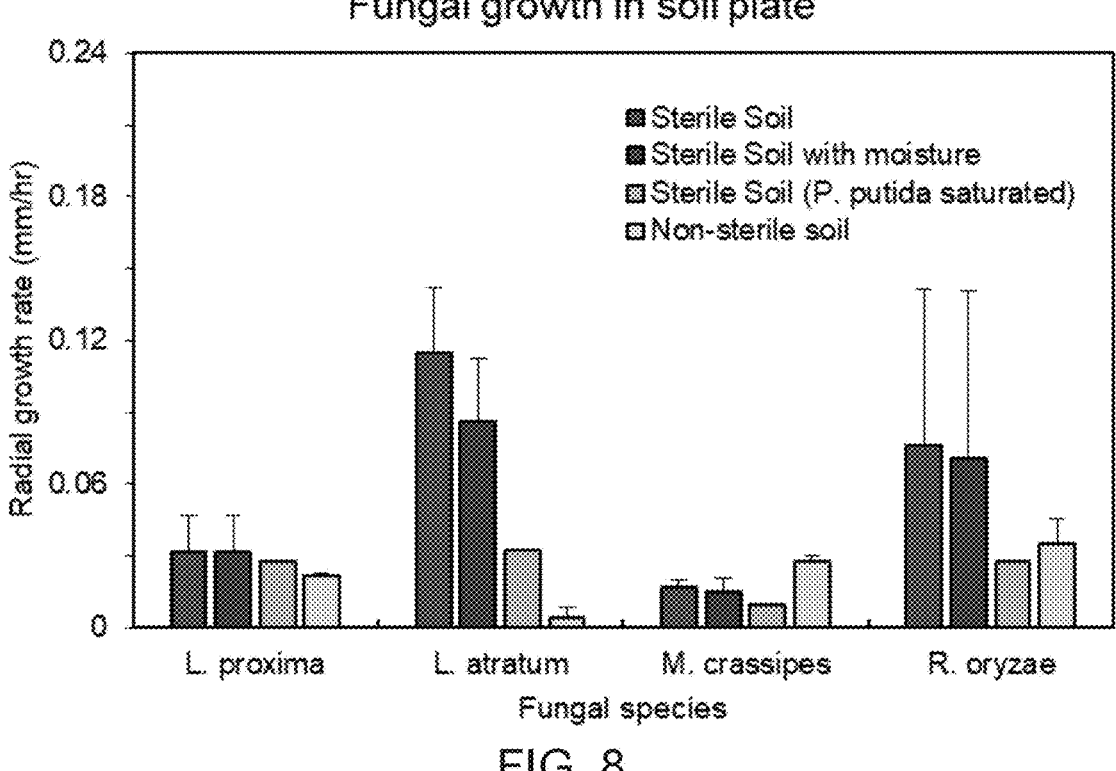
FIG. 8 is a graph of fungal growth in a horizontal soil plate.

Growth of the fungal strains was studied on the basis of their radial migration (horizontal) on the surface of OFA, PDA and soil plates from the center. Horizontal growth was measured by putting the piece of agar with fungal hyphae from the source plate at the center of destination plate followed by measuring the radial growth after every 24 h until the fungal hyphae touch the edges. The four fungal strains (*L. proxima*, *M. crassipes*, *L. atratum*, and *R. oryzae*) were grown on sterile soil, sterile soil with moisture, sterile soil that was then saturated with *P. putida*, and on non-sterile soil. The radial growth rate in mm/hr is shown in FIG. 8.

Figure 9:
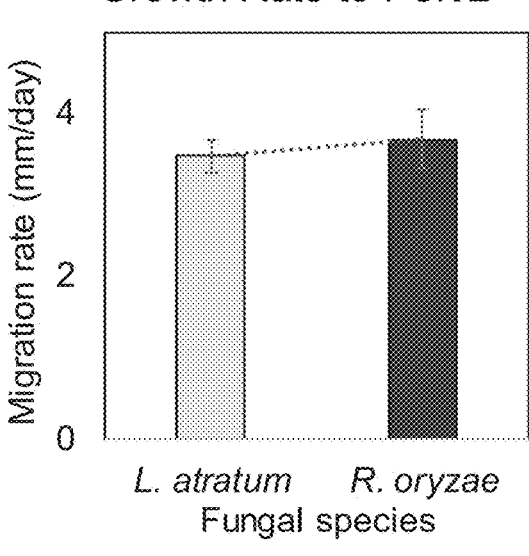
FIGS. 9-11 are graphs of fungal growth in vertical soil columns.
Figure 10:
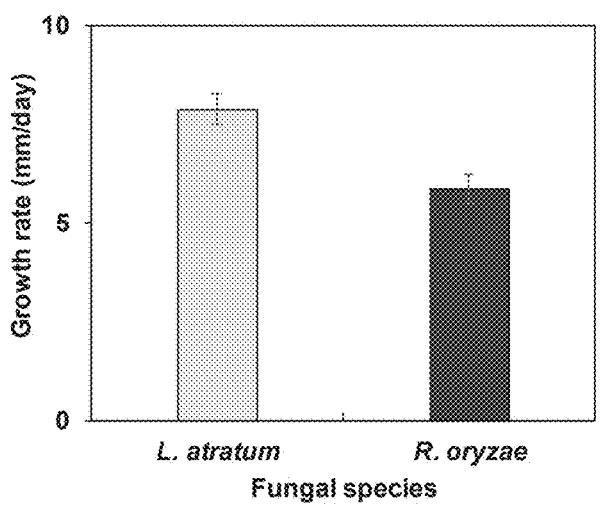
Figure 11:
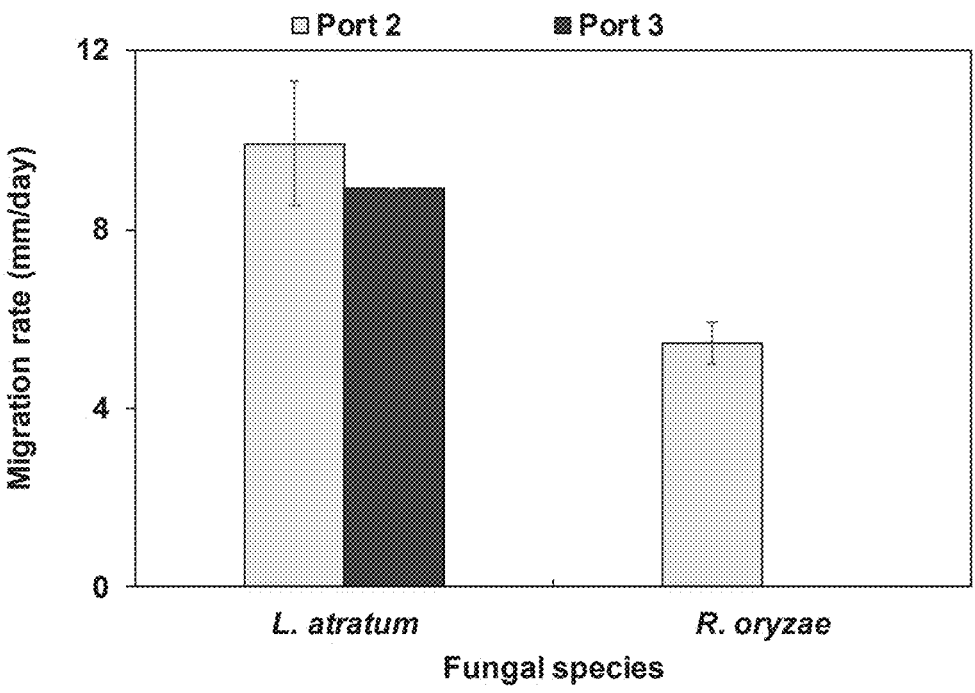

Further, the radial growth (vertical) on soil columns was also studied in the downward direction in the various scale soil columns including 80 mm, 250 mm, and 500 mm. For the vertical growth study the inoculum was prepared using the pre grown fungi on the agar plate and transferring the piece of agar to the soil plate. This soil plate was used as a source of inoculum for the further study. During the growth in soil column, soil samples (~ 30 mg) were collected from the sampling port and spread on the OFA plates. On the basis of the growth on OFA plates the growth of fungal strain was assumed. FIG. 9 shows the growth rate of *L. atratum* and *R. oryzae* in the 80 mm column and FIG. 10 shows the growth rate in the 250 mm column. FIG. 11 shows the growth rate in the 500 mm column. In this figure, "port 2" is the port located 250 mm from the top of the column, and "port 3" is the port 500 mm from the top of the column. *L. atratum* reached port 3 before *R. oryzae*.

Engineering *P. putida*

Engineered *P. putida* strains were rapidly constructed using the phage integrase-based toolkit. This toolkit enables up to 9 genomic integrations via 'landing pads' at 3 different genomic loci, each of which contains 3 attB sites. There are a total of 27 target plasmids, each with one of the 9 attP sites and one of 3 *E. coli* origin of replication and selection marker combinations. By co-transforming the target plasmid with the appropriate integrase suicide vector, integrations can be achieved at high efficiency. All plasmids were assembled using Golden Gate Assembly with BbsI to clone into the multiple cloning site common to all 27 target plasmids. This cloning method was selected for the ease by which different promoter and CDS parts could be combined combinatorically. Each assembly included the desired target plasmid as well as a promoter/RBS and CDS part. Promoter/ RBS parts were flanked by the scars: On the left, G1 (AGAAGACCTATCC), on the right C (AATGTTGTCTTCT); CDS parts were flanked by the following scars: On the left, C (AGAAGACAAAATG), on the right G2 (CTGGTTGTCTTCT). All the parts were constructed either by DNA synthesis or overhang PCR.

To limit the number of strains that would need to be assembled, only the Lux system, native to *Vibrio fischerii*, and the Las system, native to *Pseudomonas aeruginosa*, were used. These two systems yielded the strongest inducible expression in *E. coli*. The quorum sensing promoter and CDS sequences were obtained from Addgene. List of plasmid obtained from Addgene is as follows:

| Plasmid | #Addgene item number | Part obtained |
|---|---|---|
| Bsrs078-LuxR | 85142 | LuxR |
| Bsrs078-LasR | 85147 | LasR |
| Bsrs078-RpaR | 85148 | RpaR |
| Bsrs074-Plux | 85149 | Plux |
| Bsrs078-TraR | 85150 | TraR |
| Bsrs078-TraR(W) | 85151 | TraR |
| Bsrs074-Ptra | 85153 | Ptra |
| Bsrs074-Ptra* | 85154 | Ptra |
| Bsrs074-Plas | 85155 | Plas |
| Bsrs074-Prpa | 85157 | Prpa |
| Bsrs074-Prpa* | 85158 | Prpa |
| pSB1C3 I0500 LuxI | 107965 | LuxI |
| pSB1C3 I0500 LasI | 107966 | LasI |

By using all the parts described above *P. putida* has been engineered accordingly as follows:

| Strain | Plasmid | Genotype | Selection marker | Ori |
|---|---|---|---|---|
| *P. putida* AG4775 | pJH0204 and pJH0228 | pJH0204-pTacLac-mNeonGreen; pJH0228-pTacLac-LasR | Kan/Spect/Strept | |
| *P. putida* AG4775 | | pJH0204-pTacLac-mNeonGreen(-) | Kan | ColE1 |
| *P. putida* AG4775 | pJH0220-pLux-TdTomato | | Gentamicin | ColA |
| *P. putida* AG4775 | pJH0220-pLas-TdTomato | | Gentamicin | ColA |
| *P. putida* AG4775 | | pJH0204-pTacLac-mNeonGreen(-); pJH0228-pTacLac-LasR | Spectinomycin/ Streptomycin | |
| *P. putida* AG4775 | | pJH0204-pTacLac-mNeonGreen; pJH0228-pTacLac-LuxR | Kan/Spect/Strept | |
| *P. putida* AG4775 | | pJH0204-pTacLac-mNeonGreen(-); pJH0228-pTacLac-LuxR | Spectinomycin/ Streptomycin | |
| *P. putida* AG4775 | | pJH0204-pTacLac-mNeonGreen(-); pJH0228-pTacLac-LuxR; pJH0220-pLux-RBS9-TdTomato | Spect/Strept/Gent | |
| *P. putida* AG4775 | | pJH0204-pTacLac-mNeonGreen(-); pJH0228-pTacLac-LuxR; pJH0220-pLas-RBS9-TdTomato | Spect/Strept/Gent | |
| *P. putida* AG4775 | | pJH0204-pTacLac-mNeonGreen(-); pJH0228-pTacLac-LasR; pJH0220-pLux-RBS9-TdTomato | Spect/Strept/Gent | |

-continued

| Strain | Plasmid | Genotype | Selection marker | Ori |
|---|---|---|---|---|
| *P. putida* AG4775 | | pJH0204-pTacLac-mNeonGreen(-); pJH0228-pTacLac-LasR; pJH0220-pLas-RBS9-TdTomato | Spect/Strept/Gent | |
| *P. putida* AG4775 | | pJH0204-pTacLac-mNeonGreen(-); pJH0228-pTacLac-LuxR; pJH0220-pLas-RBS9-TdTomato; pJH0207-pLux-RBS13-LasI | Kan/Spect/Strept/Gent | |
| *P. putida* AG4775 | | pJH0204-pTacLac-mNeonGreen(-); pJH0228-pTacLac-LasR; pJH0220-pLux-RBS9-TdTomato; pJH0207-pLux-RBS13-LasI | Kan/Spect/Strept/Gent | |
| *P. putida* AG4775 | | pJH0204-pTacLac-mNeonGreen(-); pJH0228-pTacLac-LasR; pJH0220-pLas-RBS9-TdTomato; pJH0207-pLux-RBS13-LasI | Kan/Spect/Strept/Gent | |
| *P. putida* AG4775 | | pJH0204-pTacLac-mNeonGreen(-); pJH0228-pTacLac-LuxR; pJH0220-pLas-RBS9-TdTomato; pJH0207-pLas-RBS13-LasI | Kan/Spect/Strept/Gent | |
| *P. putida* AG4775 | | pJH0204-pTacLac-mNeonGreen(-); pJH0228-pTacLac-LasR; pJH0220-pLux-RBS9-TdTomato; pJH0207-pLas-RBS13-LasI | Kan/Spect/Strept/Gent | |
| *P. putida* AG4775 | | pJH0204-pTacLac-mNeonGreen(-); pJH0228-pTacLac-LasR; pJH0220-pLas-RBS9-TdTomato; pJH0207-pLas-RBS13-LasI | Kan/Spect/Strept/Gent | |
| *P. putida* AG4775 | pJH0207-pTet-LuxI | | Kan | |
| *P. putida* AG4775 | pJH0207-pTet-LasI | | Kan | |
| *P. putida* AG4775 | pJH0207-pLux-RBS13-LuxI | | Kan | |
| *P. putida* AG4775 | pJH0207-pLas-RBS13-LuxI | | Kan | |
| *P. putida* AG4775 | | pJH0204-pTacLac-mNeonGreen(-); pJH0228-pTacLac-LuxR; pJH0220-pLux-RBS9-TdTomato; pJH0207-pLux-RBS13-LuxI | Kan/Spect/Strept/Gent | |
| *P. putida* AG4775 | | pJH0204-pTacLac-mNeonGreen(-); pJH0228-pTacLac-LuxR; pJH0220-pLas-RBS9-TdTomato; pJH0207-pLux-RBS13-LuxI | Kan/Spect/Strept/Gent | |
| *P. putida* AG4775 | | pJH0204-pTacLac-mNeonGreen(-); pJH0228-pTacLac-LasR; pJH0220-pLux-RBS9-TdTomato; pJH0207-pLux-RBS13-LuxI | Kan/Spect/Strept/Gent | |

-continued

| Strain | Plasmid | Genotype | Selection marker | Ori |
|---|---|---|---|---|
| *P. putida* AG4775 | | pJH0204-pTacLac-mNeonGreen(-); pJH0228-pTacLac-LasR; pJH0220-pLas-RBS9-TdTomato; pJH0207-pLux-RBS13-LuxI | Kan/Spect/ Strept/Gent | |
| *P. putida* AG4775 | | pJH0204-pTacLac-mNeonGreen(-); pJH0228-pTacLac-LuxR; pJH0220-pLux-RBS9-TdTomato; pJH0207-pLas-RBS13-LuxI | Kan/Spect/ Strept/Gent | |
| *P. putida* AG4775 | | pJH0204-pTacLac-mNeonGreen(-); pJH0228-pTacLac-LuxR; pJH0220-pLas-RBS9-TdTomato; pJH0207-pLas-RBS13-LuxI | Kan/Spect/ Strept/Gent | |
| *P. putida* AG4775 | | pJH0204-pTacLac-mNeonGreen(-); pJH0228-pTacLac-LasR; pJH0220-pLux-RBS9-TdTomato; pJH0207-pLas-RBS13-LuxI | Kan/Spect/ Strept/Gent | |
| P. putida AG4775 | | pJH0204-pTacLac-mNeonGreen(-); pJH0228-pTacLac-LasR; pJH0220-pLas-RBS9-TdTomato; pJH0207-pLas-RBS13-LuxI | Kan/Spect/ Strept/Gent | |
| *P. putida* AG4775 | pJH0204-pTacLac-TetR | | Kan | ColE1 |
| *P. putida* AG4775 | | pJH0204-pTacLac-TetR | Kan | |
| *P. putida* AG4775 | | pJH0204-pTacLac-TetR(-) | Kan | |
| *P. putida* AG4775 | | pJH0204-pTacLac-TetR(-); pJH0228-pTacLac-LuxR | Spect/Strept | |
| *P. putida* AG4775 | | pJH0204-pTacLac-TetR(-); pJH0228-pTacLac-LasR | Spect/Strept | |
| *P. putida* AG4775 | | pJH0204-pTacLac-TetR(-); pJH0228-pTacLac-LuxR; pJH0220-pLux-RBS9-TdTomato | Spect/Strept/Gent | |
| *P. putida* AG4775 | | pJH0204-pTacLac-TetR(-); pJH0228-pTacLac-LuxR; pJH0220-pLas-RBS9-TdTomato | Spect/Strept/Gent | |
| *P. putida* AG4775 | | pJH0204-pTacLac-TetR(-); pJH0228-pTacLac-LasR; pJH0220-pLux-RBS9-TdTomato | Spect/Strept/Gent | |
| *P. putida* AG4775 | | pJH0204-pTacLac-TetR(-); pJH0228-pTacLac-LasR; pJH0220-pLas-RBS9-TdTomato | Spect/Strept/Gent | |
| *P. putida* AG4775 | | pJH0204-pTacLac-TetR(-); pJH0228-pTacLac-LuxR; pJH0220-pLux-RBS9-TdTomato; pJH0207-pTet-RBS13-LasI | Kan/Spect/ Strept/Gent | |
| *P. putida* AG4775 | | pJH0204-pTacLac-TetR(-); pJH0228-pTacLac-LasR; pJH0220-pLux-RBS9- | Kan/Spect/ Strept/Gent | |

-continued

| Strain | Plasmid | Genotype | Selection marker | Ori |
|---|---|---|---|---|
| P. putida AG4775 | | TdTomato; pJH0207-pTet-RBS13-LuxI pJH0204-pTacLac-TetR(-); pJH0228-pTacLac-LasR; pJH0220-pLux-RBS9-TdTomato; pJH0207-pTet-RBS13-LasI | Kan/Spect/Strept/Gent | |
| P. putida AG4775 | | pJH0204-pTacLac-TetR(-); pJH0228-pTacLac-LuxR; pJH0220-pLas-RBS9-TdTomato; pJH0207-pTet-RBS13-LuxI | Kan/Spect/Strept/Gent | |
| | | pJH0204-pTacLac-TetR(-); pJH0228-pTacLac-LuxR; pJH0220-pLas-RBS9-TdTomato; pJH0207-pTet-RBS13-LasI | Kan/Spect/Strept/Gent | |
| P. putida AG4775 | | pJH0204-pTacLac-TetR(-); pJH0228-pTacLac-LasR; pJH0220-pLas-RBS9-TdTomato; pJH0207-pTet-RBS13-LuxI | Kan/Spect/Strept/Gent | |
| P. putida AG4775 | | pJH0204-pTacLac-TetR(-); pJH0228-pTacLac-LasR; pJH0220-pLas-RBS9-TdTomato; pJH0207-pTet-RBS13-LasI | Kan/Spect/Strept/Gent | |
| P. putida AG4775 | pJH0216-pTacLac-sfGFP-tag | | Gentamicin | ColA |
| P. putida AG4775 | pJH0228-pTacLac-T7RNAP | | Spect/Strept | CloDF13 |
| P. putida AG4775 | pJH0204-pT7-RBS13-mNeonGreen | | Kan | ColE1 |
| P. putida AG4775 | | pJH0204-pTacLac-TetR(-); pJH0228-pTacLac-LuxR; pJH0207-pLux-RBS13-LuxI | Spect/Strept/Kan | |
| P. putida AG4775 | | pJH0204-pTacLac-TetR(-); pJH0228-pTacLac-LasR; pJH0207-pLux-RBS13-LuxI | Spect/Strept/Kan | |
| P. putida AG4775 | | pJH0204-pTacLac-TetR(-); pJH0228-pTacLac-LuxR; pJH0207-pLas-RBS13-LasI | Spect/Strept/Kan | |
| P. putida AG4775 | | pJH0204-pTacLac-TetR(-); pJH0228-pTacLac-LasR; pJH0207-pLas-RBS13-LasI | Spect/Strept/Kan | |
| P. putida AG4775 | | pJH0204-pTacLac-TetR(-); pJH0228-pTacLac-LuxR; pJH0207-pLux-RBS13-LasI | Spect/Strept/Kan | |
| P. putida AG4775 | | pJH0204-pTacLac-TetR(-); pJH0228-pTacLac-LasR; pJH0207-pLux-RBS13-LasI | Spect/Strept/Kan | |
| P. putida AG4775 | | pJH0204-pTacLac-TetR(-); pJH0228-pTacLac-LuxR; pJH0207-pLas-RBS13-LuxI | Spect/Strept/Kan | |

-continued

| Strain | Plasmid | Genotype | Selection marker | Ori |
|---|---|---|---|---|
| *P. putida* AG4775 | | pJH0204-pTacLac-TetR(-); pJH0228-pTacLac-LasR; pJH0207-pLas-RBS13-LuxI | Spect/Strept/Kan | |
| *P. putida* AG4775 | | pJH0211-pTet-RBS13-LuxI | Kanamycin | ColE1 |
| *P. putida* AG4775 | | pJH0211-pTet-RBS13-LasI | Kanamycin | ColE1 |
| *P. putida* AG4775 | | pJH0204-pTacLac-TetR(-), pJH0228-pTacLac-LasR, pJH0207-pLux-RBS13-LuxI, pJH0211-pTet-RBS13-LuxI | Spect/Strept/Kan | |
| *P. putida* AG4775 | | pJH0204-pTacLac-TetR(-), pJH0228-pTacLac-LasR, pJH0207-pLux-RBS13-LuxI, pJH0211-pTet-RBS13-LasI | Spect/Strept/Kan | |
| *P. putida* AG4775 | | pJH0204-pTacLac-TetR(-), pJH0228-pTacLac-LuxR, pJH0207-pLux-RBS13-LuxI, pJH0211-pTet-RBS13-LuxI | Spect/Strept/Kan | |
| *P. putida* AG4775 | | pJH0204-pTacLac-TetR(-), pJH0228-pTacLac-LuxR, pJH0207-pLux-RBS13-LuxI, pJH0211-pTet-RBS13-LasI | Spect/Strept/Kan | |
| *P. putida* AG4775 | | pJH0204-pTacLac-TetR(-), pJH0228-pTacLac-LasR, pJH0207-pLas-RBS13-LasI, pJH0211-pTetRBS13-LuxI | Spect/Strept/Kan | |
| *P. putida* AG4775 | | pJH0204-pTacLac-TetR(-), pJH0228-pTacLac-LasR, pJH0207-pLas-RBS13-LasI, pJH0211-pTetRBS13-LasI | Spect/Strept/Kan | |
| *P. putida* AG4775 | | pJH0204-pTacLac-TetR(-), pJH0228-pTacLac-LuxR, pJH0207-pLas-RBS13-LasI, pJH0211-pTet-RBS13-LuxI | Spect/Strept/Kan | |
| *P. putida* AG4775 | | pJH0204-pTacLac-TetR(-), pJH0228-pTacLac-LuxR, pJH0207-pLas-RBS13-LasI, pJH0211-pTet-RBS13-LasI | Spect/Strept/Kan | |
| *P. putida* AG4775 | | pJH0204-pTacLac-TetR(-), pJH0228-pTacLac-LasR, pJH0207-pLux-RBS13-LasI, pJH0211-pTet-RBS13-LuxI | Spect/Strept/Kan | |

-continued

| Strain | Plasmid | Genotype | Selection marker | Ori |
|---|---|---|---|---|
| *P. putida* AG4775 | | pJH0204-pTacLac-TetR(-), pJH0228-pTacLac-LasR, pJH0207-pLux-RBS13-LasI, pJH0211-pTet-RBS13-LasI | Spect/Strept/Kan | |
| *P. putida* AG4775 | | pJH0204-pTacLac-TetR(-), pJH0228-pTacLac-LuxR, pJH0207-pLux-RBS13-LasI, pJH0211-pTet-RBS13-LuxI | Spect/Strept/Kan | |
| *P. putida* AG4775 | | pJH0204-pTacLac-TetR(-), pJH0228-pTacLac-LuxR, pJH0207-pLux-RBS13-LasI, pJH0211-pTet-RBS13-LasI | Spect/Strept/Kan | |
| *P. putida* AG4775 | | pJH0204-pTacLac-TetR(-), pJH0228-pTacLac-LasR, pJH0207-pLas-RBS13-LuxI, pJH0211-pTet-RBS13-LuxI | Spect/Strept/Kan | |
| *P. putida* AG4775 | | pJH0204-pTacLac-TetR(-), pJH0228-pTacLac-LasR, pJH0207-pLas-RBS13-LuxI, pJH0211-pTet-RBS13-LasI | Spect/Strept/Kan | |
| *P. putida* AG4775 | | pJH0204-pTacLac-TetR(-), pJH0228-pTacLac-LuxR, pJH0207-pLas-RBS13-LuxI, pJH0211-pTet-RBS13-LuxI | Spect/Strept/Kan | |
| *P. putida* AG4775 | | pJH0204-pTacLac-TetR(-), pJH0228-pTacLac-LuxR, pJH0207-pLas-RBS13-LuxI, pJH0211-pTet-RBS13-LasI | Spect/Strept/Kan | |

The resulting *P. putida* organisms include the following DNA sequences of functional genetic circuits integrated therein:

pTacLac-mNeonGreen:

(SEQ ID: NO 1)

GATCCGAGCTGTTGACAATTAATCATCGGCTCGTATAATGTGTGGAATTG

TGAGCGGATAACAATTTCACACAGGAAACAGAATCATATGGTCAGCAAAG

GCGAAGAAGACAACATGGCTTCCCTCCCGGCTACGCACGAACTGCACATC

TTTGGCAGCATCAATGGCGTGGACTTTGACATGGTCGGTCAAGGCACCGG

TAACCCGAACGACGGCTACGAGGAGCTGAACCTGAAGAGCACGAAGGGGG

ACCTCCAGTTCAGCCCTTGGATTCTGGTGCCCCACATTGGTTACGGTTTC

CATCAGTACCTGCCGTACCCGGACGGCATGTCCCCATTCCAGGCCGCAAT

GGTGGATGGCAGCGGCTACCAAGTTCACCGTACCATGCAGTTTGAGGACG

GGGCGAGTTTGACCGTTAATTACCGCTACACCTATGAGGGCTCCCATATC

-continued

AAGGGTGAAGCCCAAGTAAAGGGCACCGGCTTTCCTGCGGACGGGCCCGT

GATGACCAACTCGCTGACCGCGGCCGATTGGTGTCGTTCCAAAAAGACGT

ATCCGAACGACAAGACCATCATCAGTACCTTTAAGTGGAGCTACACCACC

GGGAACGGCAAGCGCTATCGTTCGACGGCGCGCACGACCTACACGTTCGC

TAAGCCGATGGCCGCCAACTATCTCAAGAACCAGCCAATGTACGTGTTCC

GCAAAACCGAGTTGAAGCACTCGAAGACCGAACTGAACTTCAAGGAATGG

CAGAAGGCGTTCACGGACGTGATGGGCATGGACGAGCTGTATAAGGACTA

CAAGGACGATGACGACAAGTAA pLas-LuxI:

(SEQ ID: NO 2)

ATCCTTCGAGCCTAGCAAGGGTCGGGGTTCACCGAAATCTATCTCATTTG

CTAGTTATAAAATTATGAAATTTGCGTAAATTCTTCAGAAAGAATCCTAT

CCCAATAAGGAGGTATATTAATGACTATAATGATAAAAAAATCGGATTTT

-continued

```
TTGGCAATTCCATCGGAGGAGTATAAAGGTATTCTAAGTCTCCGTTATCA

AGTGTTTAAGCAAAGACTTGAGTGGGACTTAGTTGTAGAAAATAACCTTG

AATCAGATGAGTATGATAACTCAAATGCAGAATATATTTATGCTTGTGAT

GATACTGAAAATGTAAGTGGATGCTGGCGTTTATTACCTACAACAGGTGA

TTATATGCTGAAAAGTGTTTTTCCTGAATTGCTTGGTCAACAGAGTGCTC

CCAAAGATCCTAATATAGTCGAATTAAGTCGTTTTGCTGTAGGTAAAAAT

AGCTCAAAGATAAATAACTCTGCTAGTGAAATTACAATGAAACTATTTGA

AGCTATATATAAACACGCTGTTAGTCAAGGTATTACAGAATATGTAACAG

TAACATCAACAGCAATAGAGCGATTTTTAAAGCGTATTAAAGTTCCTTGT

CATCGTATTGGAGACAAAGAAATTCATGTATTAGGTGATACTAAATCGGT

TGTATTGTCTATGCCTATTAATGAACAGTTTAAAAAAGCAGTCTTAAATT

AATCTGG
``` pLux-LuxI:

(SEQ ID: NO 3)
```
ATCCACTATTGTATCGCTGGGAATACAATTACTTAACATAAGCACCTGTA

GGATCGTACAGGTTTACGCAAGAAATGGTTTGTTATAGTCGAATATGAA

AGAATCCTATCCCAATAAGGAGGTATATTAATGAAAAACATAAATGCCGA

CGACACATACAGAATAATTAATAAAATTAAAGCTTGTAGAAGCAATAATG

ATATTAATCAATGCTTATCTGATATGACTAAAATGGTACATTGTGAATAT

TATTTACTCGCGATCATTTATCCTCATTCTATGGTTAAATCTGATATTTC

AATTCTAGATAATTACCCTAAAAAATGGAGGCAATATTATGATGACGCTA

ATTTAATAAAATATGATCCTATAGTAGATTATTCTAACTCCAATCATTCA

CCAATTAATTGGAATATATTTGAAAACAATGCTGTAAATAAAAAATCTCC

AAATGTAATTAAAGAAGCGAAAACATCAGGTCTTATCACTGGGTTTAGTT

TCCCTATTCATACGGCTAACAATGGCTTCGGAATGCTTAGTTTTGCACAT

TCAGAAAAAGACAACTATATAGATAGTTTATTTTTACATGCGTGTATGAA

CATACCATTAATTGTTCCTTCTCTAGTTGATAATTATCGAAAAATAAATA

TAGCAAATAATAAATCAAACAACGATTTAACCAAAAGAGAAAAAGAATGT

TTAGCGTGGGCATGCGAAGGAAAAAGCTCTTGGGATATTTCAAAAATATT

AGGCTGCAGTGAGCGTACTGTCACTTTCCATTTAACCAATGCGCAAATGA

AACTCAATACAACAAACCGCTGCCAAAGTATTTCTAAAGCAATTTTAACA

GGAGCAATTGATTGCCCATACTTTAAAAATTAAGCTGG
``` pLas-LasI:

(SEQ ID: NO 4)
```
ATCCTTCGAGCCTAGCAAGGGTCCCGGGTTCACCGAAATCTATCTCATTTG

CTAGTTATAAAATTATGAAATTTGCGTAAATTCTTCAGAAAGAATCCTAT

CCCAATAAGGAGGTATATTAATGATTGTTCAGATTGGCCGTCGTGAGGAA

TTTGATAAAAAGCTGCTGGGCGAGATGCACAAACTGCGTGCACAGGTTTT

CAAGGAGCGTAAAGGTTGGGACGTTAGCGTTATTGACGAAATGGAGATTG

ATGGCTACGACGCTCTGTCTCCGTATTATATGCTGATTCAGGAGGACACC

CCGGAAGCTCAGGTATTTGGTTGCTGGCGTATCTTCGATACTACGGGTCC

GTATATGCTGAAAAATACCTTCCCGGAACTGCTGCACGGTAAAGAAGCGC
```

-continued

```
CTTGTAGCCCGCACATCTGGGAACTGTCTCGTTTCGCTATCAACTCCGGC

CAGAAAGGTTCCCTGGGCTTTTCCGATTGTACCCTGGAAGCAATGCGTGC

GCTGGCGCGCTATTCACTGCAAAACGACATCCAGACTCTGGTGACCGTTA

CTACTGTGGGCGTTGAAAAGATGATGATCCGTGCAGGCCTGGACGTTAGC

CGTTTCGGTCCACACCTGAAGATCGGTATCGAACGCGCGGTGGCCCTGCG

TATCGAACTGAATGCAAAAACCCAGATCGCACTGTATGGTGGTGTTCTGG

TGGAACAACGCCTGGCCGTTTCCTAATAATCTGG
``` pLux-LasI:

(SEQ ID: NO 5)
```
ATCCACTATTGTATCGCTGGGAATACAATTACTTAACATAAGCACCTGTA

GGATCGTACAGGTTTACGCAAGAAATGGTTTGTTATAGTCGAATATGAA

AGAATCCTATCCCAATAAGGAGGTATATTAATGATTGTTCAGATTGGCCG

TCGTGAGGAATTTGATAAAAAGCTGCTGGGCGAGATGCACAAACTGCGTG

CACAGGTTTTCAAGGAGCGTAAAGGTTGGGACGTTAGCGTTATTGACGAA

ATGGAGATTGATGGCTACGACGCTCTGTCTCCGTATTATATGCTGATTCA

GGAGGACACCCCGGAAGCTCAGGTATTTGGTTGCTGGCGTATCTTCGATA

CTACGGGTCCGTATATGCTGAAAAATACCTTCCCGGAACTGCTGCACGGT

AAAGAAGCGCCTTGTAGCCCGCACATCTGGGAACTGTCTCGTTTCGCTAT

CAACTCCGGCCAGAAAGGTTCCCTGGGCTTTTCCGATTGTACCCTGGAAG

CAATGCGTGCGCTGGCGCGCTATTCACTGCAAAACGACATCCAGACTCTG

GTGACCGTTACTACTGTGGGCGTTGAAAAGATGATGATCCGTGCAGGCCT

GGACGTTAGCCGTTTCGGTCCACACCTGAAGATCGGTATCGAACGCGCGG

TGGCCCTGCGTATCGAACTGAATGCAAAAACCCAGATCGCACTGTATGGT

GGTGTTCTGGTGGAACAACGCCTGGCCGTTTCCTAATAAGCTGGT
``` pLux-RBS9-TdTomato:

(SEQ ID: NO 6)
```
ATCCACTATTGTATCGCTGGGAATACAATTACTTAACATAAGCACCTGTA

GGATCGTACAGGTTTACGCAAGAAATGGTTTGTTATAGTCGAATATTAT

AATAAGTAATTCTTAAGGGGGTAAGTCCAATGGTATCCAAGGGCGAAGAG

GTGATCAAGGAATTTATGCGCTTCAAGGTGCGCATGGAAGGCTCCATGAA

CGGCCATGAATTCGAGATTGAAGGCGAAGGTGAAGGCCGCCCCTACGAAG

GTACCCAGACGGCCAAGTTGAAGGTCACCAAGGGTGGCCCTCTGCCTTTC

GCGTGGGACATCCTGAGCCCACAGTTCATGTATGGGAGCAAGGCTTACGT

TAAACACCCGGCCGATATCCCGGACTATAAGAAGCTCAGTTTTCCTGAAG

GGTTCAAGTGGGAACGCGTGATGAATTTCGAGGATGGTGGCCTCGTAACC

GTCACCCAAGACAGCAGCCTGCAGGATGGCACCCTGATCTACAAGGTAAA

AATGCGCGGCACGAACTTCCCTCCAGATGGTCCGGTTATGCAAAAAAAGA

CCATGGGCTGGGAAGCCTCGACCGAGCGTCTGTACCCTCGTGACGGCGTG

CTCAAGGGCGAAATCCATCAAGCCCTGAAACTGAAGGATGGCGGCCATTA

CCTGGTCGAGTTCAAAACCATCTATATGGCTAAAAAGCCAGTACAGCTGC

CGGGGTATTACTATGTTGACACGAAACTCGATATTACCTCCCACAATGAG

GACTACACCATCGTGGAACAGTACGAACGCAGCGAAGGCCGTCATCATCT

CTTTCTCGGCCATGGTACCGGCTCGACGGGGTTCCGGCAGCAGCGGCACCG
```

```
-continued

CCAGCAGCGAGGACAACAATATGGCTGTCATCAAAGAGTTCATGCGTTTC

AAAGTGCGCATGGAGGGTAGCATGAATGGGCACGAATTTGAAATCGAAGG

GGAAGGTGAAGGCCGTCCGTATGAGGGCACGCAGACCGCAAAATTGAAGG

TGACGAAGGGTGGCCCCTTGCCATTTGCTTGGGACATTTTGAGCCCGCAG

TTCATGTACGGTTCCAAGGCATACGTGAAACATCCAGCTGACATCCCTGA

TTACAAGAAGCTGAGTTTCCCGGAGGGTTTTAAATGGGAACGGGTTATGA

ATTTCGAGGACGGCGGCCTGGTAACGGTCACCCAGGATTCCAGCCTGCAA

GACGGCACCCTCATTTACAAAGTGAAGATGCGTGGGACCAACTTCCCGCC

GGATGGCCCTGTTATGCAGAAGAAAACCATGGGCTGGGAAGCGTCGACCG

AGCGCCTCTACCCGCGCGACGGCGTACTGAAGGGGGAGATCCACCAGGCC

CTGAAGCTGAAGGACGGTGGTCATTACCTGGTGGAGTTCAAGACCATTTA

TATGGCCAAAAAGCCTGTTCAGTTGCCGGGCTACTACTACGTCGACACCA

AGCTCGACATCACCAGCCACAACGAGGACTACACCATTGTGGAGCAGTAC

GAGCGCAGCGAAGGCCGGCACCCACTTGTTCTTGTATGGCATGGACGAACT

GTACAAAGACTACAAGGACGACGATGACAAATAA pTacLac-LuxR:
                                        (SEQ ID: NO 7)
GAGCTGTTGACAATTAATCATCGGCTCGTATAATGTGTGGAATTGTGAGC

GGATAACAATTTCACACAGGAAACAGAATCATAATGAAAAACATAAATGC

CGACGACACATACAGAATAATTAATAAAATTAAAGCTTGTAGAAGCAATA

ATGATATTAATCAATGCTTATCTGATATGACTAAAATGGTACATTGTGAA

TATTATTTACTCGCGATCATTTATCCTCATTCTATGGTTAAATCTGATAT

TTCAATTCTAGATAATTACCCTAAAAAATGGAGGCAATATTATGATGACG

CTAATTTAATAAAATATGATCCTATAGTAGATTATTCTAACTCCAATCAT

TCACCAATTAATTGGAATATATTTGAAACAATGCTGTAAATAAAAAATC

TCCAAATGTAATTAAAGAAGCGAAAACATCAGGTCTTATCACTGGGTTTA

GTTTCCCTATTCATACGGCTAACAATGGCTTCGGAATGCTTAGTTTTGCA

CATTCAGAAAAAGACAACTATATAGATAGTTTATTTTTACATGCGTGTAT

GAACATACCATTAATTGTTCCTTCTCTAGTTGATAATTATCGAAAAATAA

ATATAGCAAATAATAAATCAAACAACGATTTAACCAAAAGAGAAAAAGAA

TGTTTAGCGTGGGCATGCGAAGGAAAAAGCTCTTGGGATATTTCAAAAAT

ATTAGGCTGCAGTGAGCGTACTGTCACTTTCCATTTAACCAATGCGCAAA

TGAAACTCAATACAACAAACCGCTGCCAAAGTATTTCTAAAGCAATTTTA

ACAGGAGCAATTGATTGCCCATACTTTAAAAATTAAGCTGGT
```

Migration of *P. putida* in Soil

Figure 12:
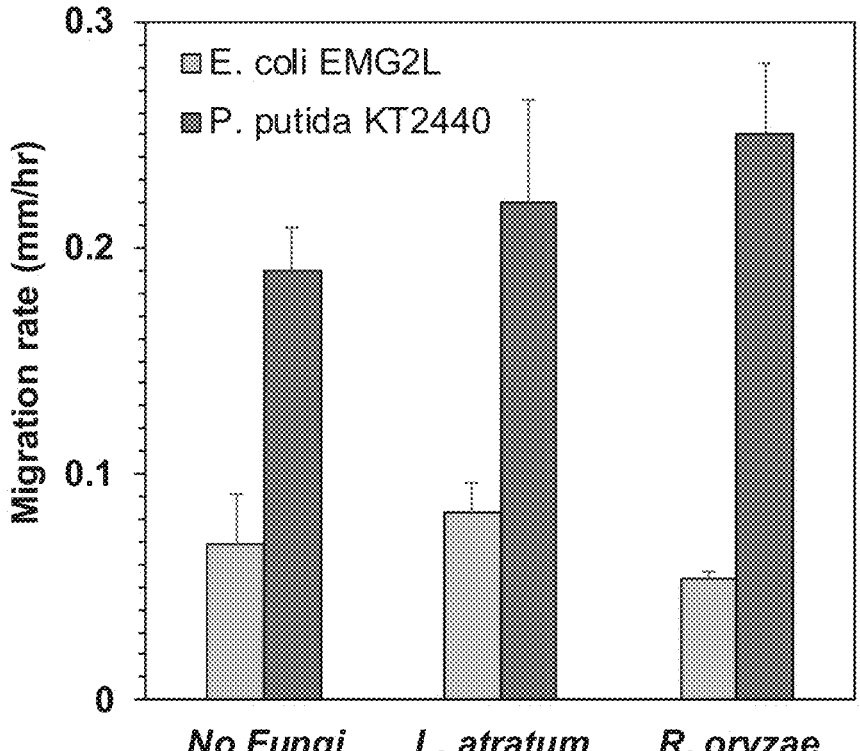
FIG. 12 is a graph of bacteria migration rate through soil columns.

Migration of *P. putida* in soil were studied using soil column with and without fungal hyphae. Inoculum of *P. putida* strain integrated with mNeon green has been prepared by growing it in 25 ml LB media for overnight followed by concentrated to $OD_{600}$ 5. Volume of 0.5, 5, and 5 ml inoculum was added on the top of the 80, 250 and 500 mm soil column with and without fungal hyphae (*L. atratum* and *R. oryzae*). During the bacterial migration ~30 mg samples were collected from the sampling port and resuspended in 500 μl phosphate buffer saline. The samples were then prepared for flow cytometric analysis. The migration rate of *P. putida* in the soil in the 80 mm soil columns is shown in FIG. 12. The same experiment was performed with *E. coli* for comparison.

Testing Inducible System in *P. putida*

Figure 13:
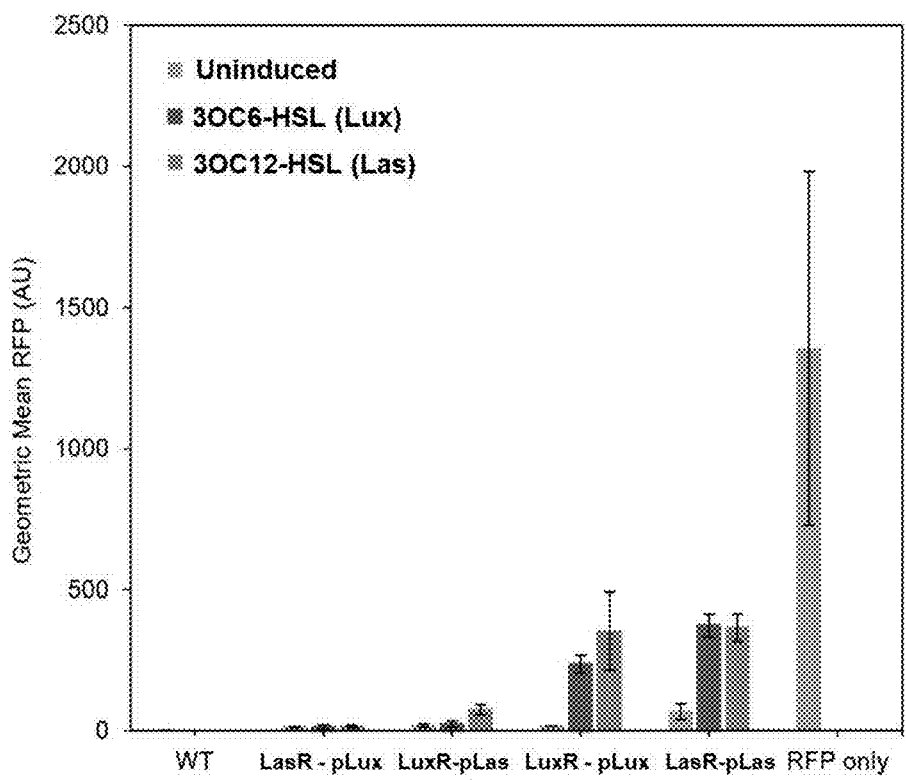
FIG. 13 is a graph of fluorescence of engineered bacteria in the presence of O3-C6-HSL and O3-C12-HSL.
Figure 14:
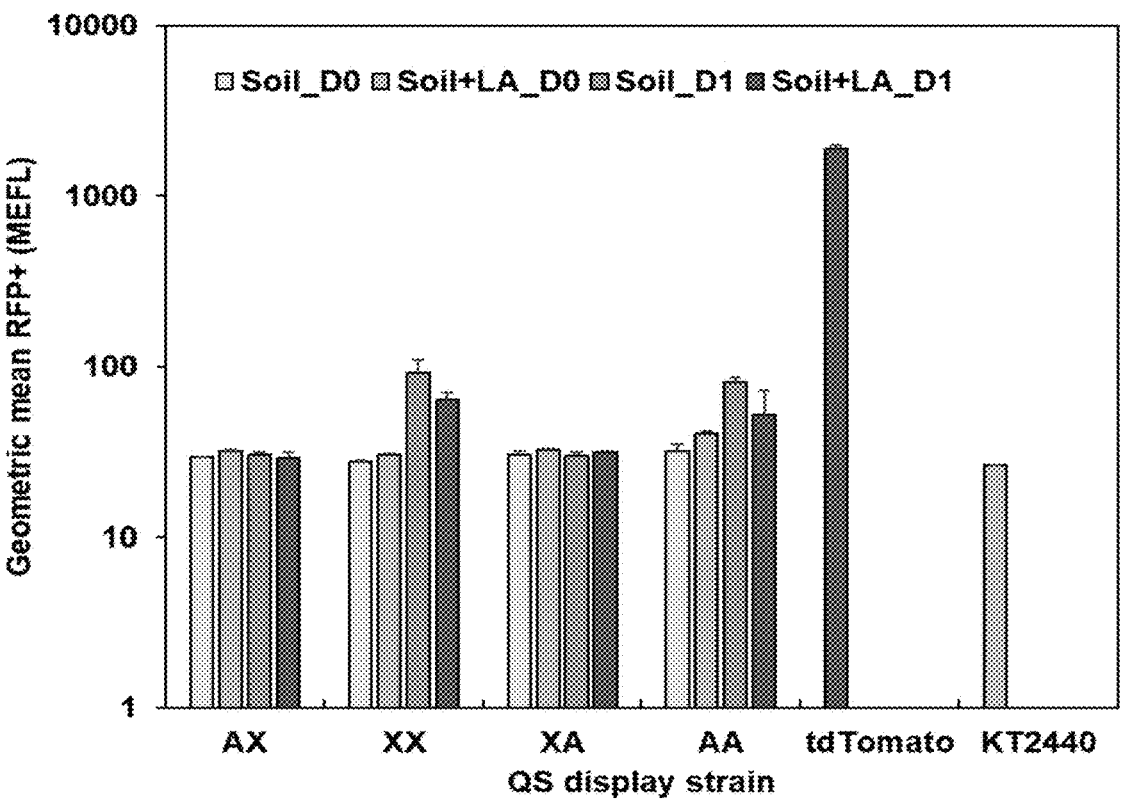
FIGS. 14-15 are graphs of fluorescence of engineered bacteria in soil in the presence of O3-C6-HSL and O3-C12-HSL.
Figure 15:
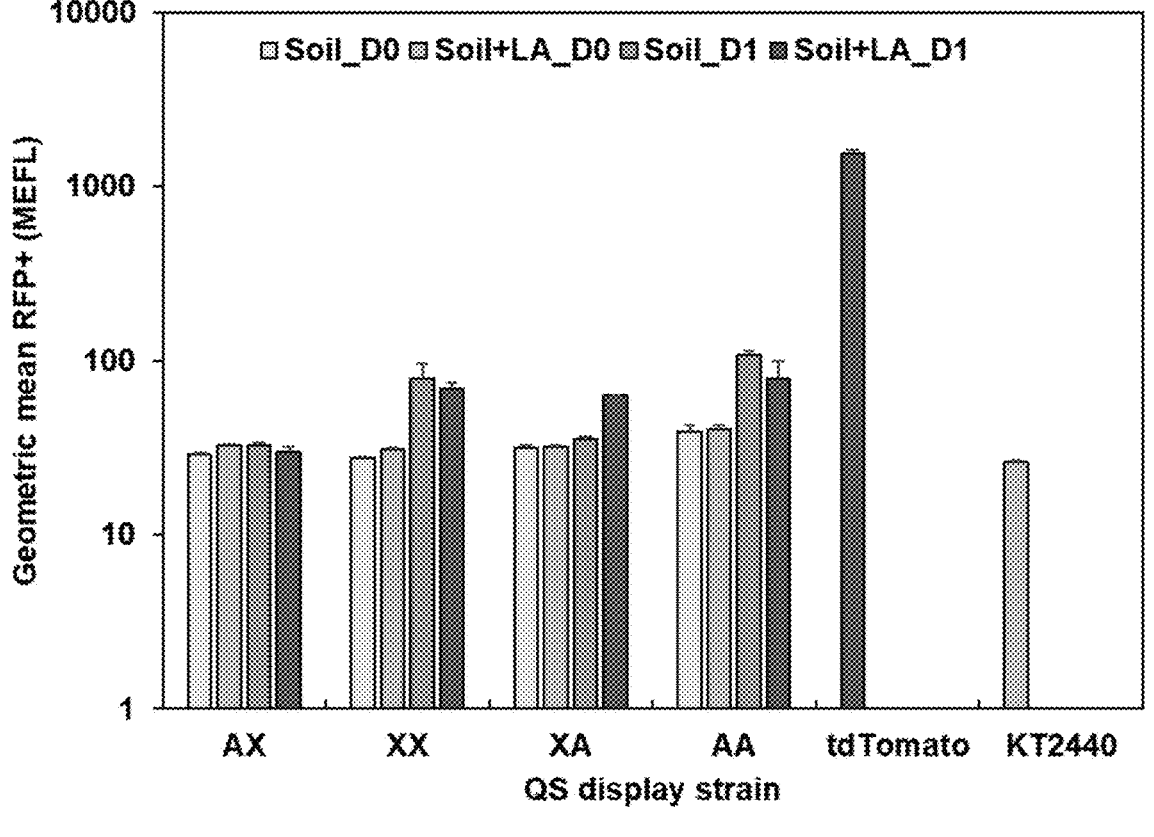

*P. putida* AG4775 has been has been engineered for various inducible system including quorum sensing and feed forward quorum sensing system. Before testing the inducible expression in soil. *P. putida* were tested on LB, M9 and soil extract liquid media. To do the testing cell were grown overnight followed by diluted to $OD_{600}$ 0.1 and induced with 10 mM Lux-HSL (O3-C6-HSL) or Las-HSL (O3-C12-HSL) and Di-methyl sulfonate as control. *P. putida* cells expresses red fluorescence protein TdTomato in response to the HSL and the fluorescence was measured using flow cytometer. FIG. 13 shows the fluorescence of each bacterial strain with either O3-C6-HSL or O3-C12-HSL. Four engineered bacterial strains were used, having the four possible combinations of the two genes LuxR and LasR and the two promoters Plus and Plas connected to the TdTomato gene for outputting red fluorescent protein. FIG. 14 shows the fluorescence results of the same experiment performed in soil, with and without fungus, at an initial time "Day 0" and after a day at time "Day 1." FIG. 14 shows the results for the experiment using 3O-C6-HSL and FIG. 15 shows the results for the experiment using 3O-C12-HSL.

Quorum Sensing in Soil

To enable *P. putida* strain to send a signal in soil in response to detectable molecules, quorum sensing was used as a way of communication between sensor and reporter strains. To detect a signals in soil, a small scale soil column was saturated with *L. atratum* and reporter strain. Further the Acyl-homoserine lactone (AHL) inducible molecule was added it the bottom of the soil column to induce the feed forward system. The propagation in the signal was tracked by collecting the soil from the sampling ports after every 24 hr of duration until the signal was propagated to the top of the soil column. Collected samples were further analyzed using the method described earlier for flow cytometric analysis.

Figure 16:
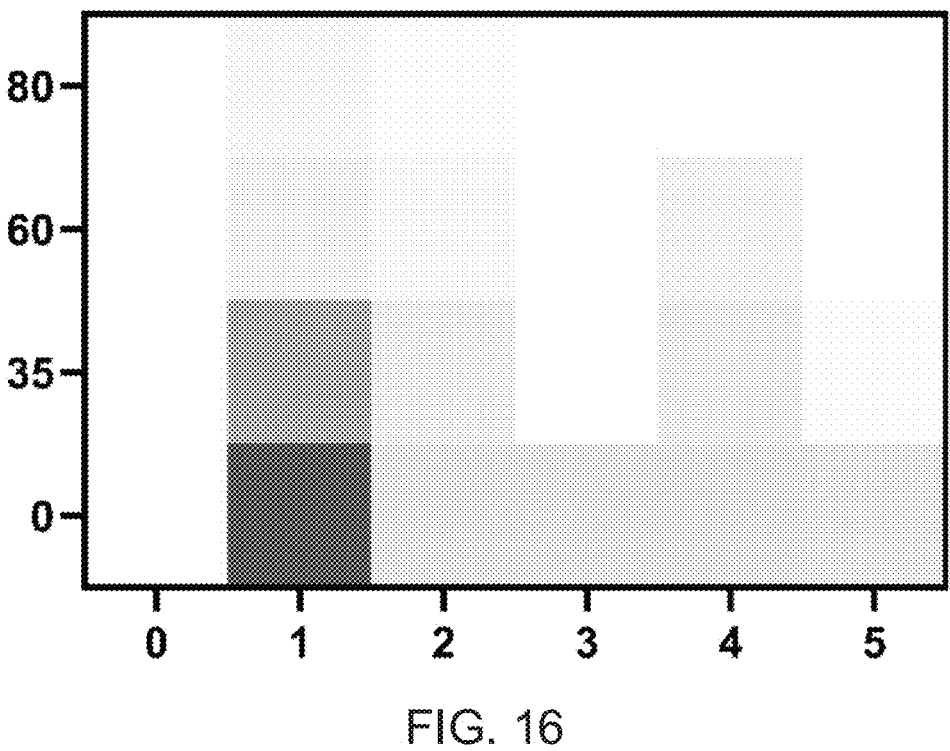
FIGS. 16-23 are heat maps of fluorescence of bacteria at different heights in a soil column over multiple days.
Figure 17:
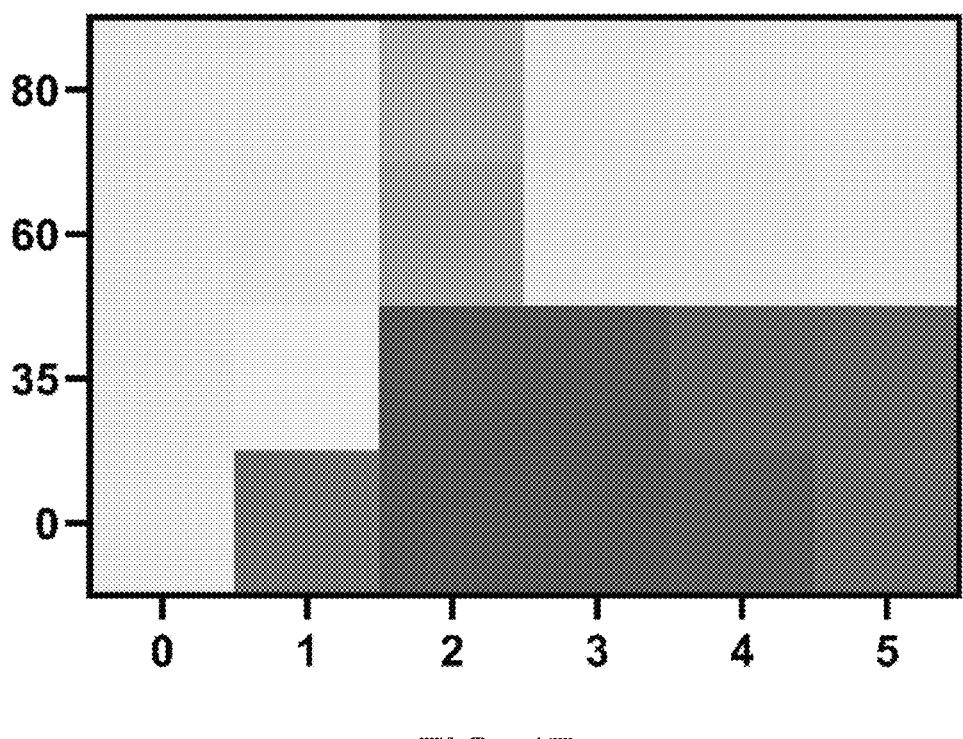

FIG. 16 is a heat map showing the relative fluorescence measured from the soil samples taken every 24 hr (shown as days on the x-axis) at different heights in the column (shown as mm on the y-axis). FIG. 16 shows the results of the experiment in soil without fungus. FIG. 17 shows the results of the same experiment in soil with fungus. The experiments in FIGS. 16 and 17 both used the strain of *P. putida* that was engineered to implement the genetic circuit shown in FIG. 4.

Figure 18:
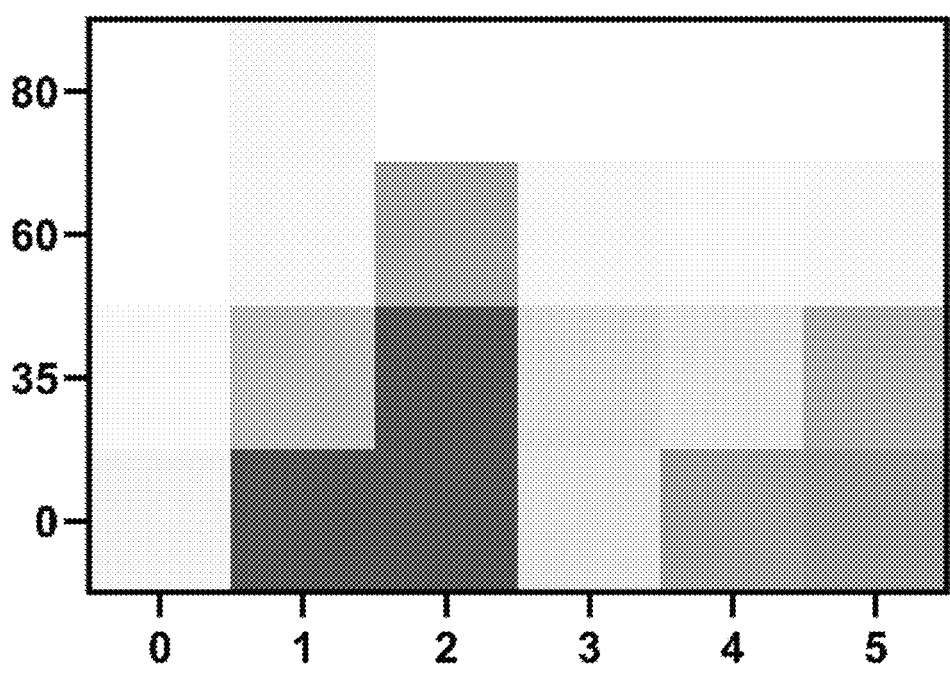
Figure 19:
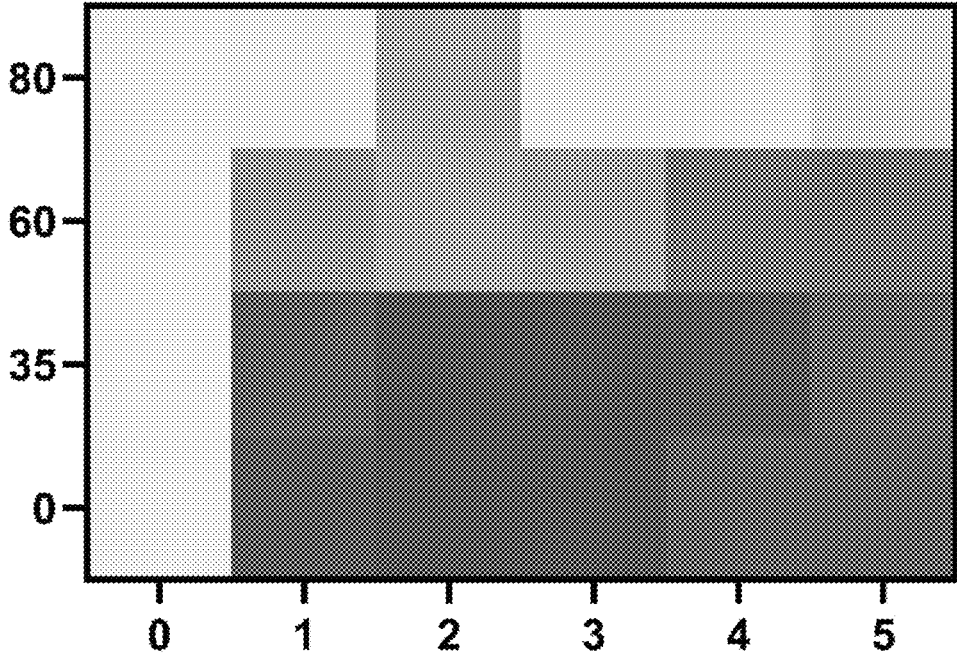

FIGS. 18 and 19 are heat maps showing the results of the same experiment using the same strain of *P. putida*, but with 3O-C6-HSL as the input as shown in the genetic circuit of FIG. 5. FIG. 18 shows the results of the experiment in soil without fungus, and FIG. 19 shows the results of the experiment in soil with fungus.

Figure 20:
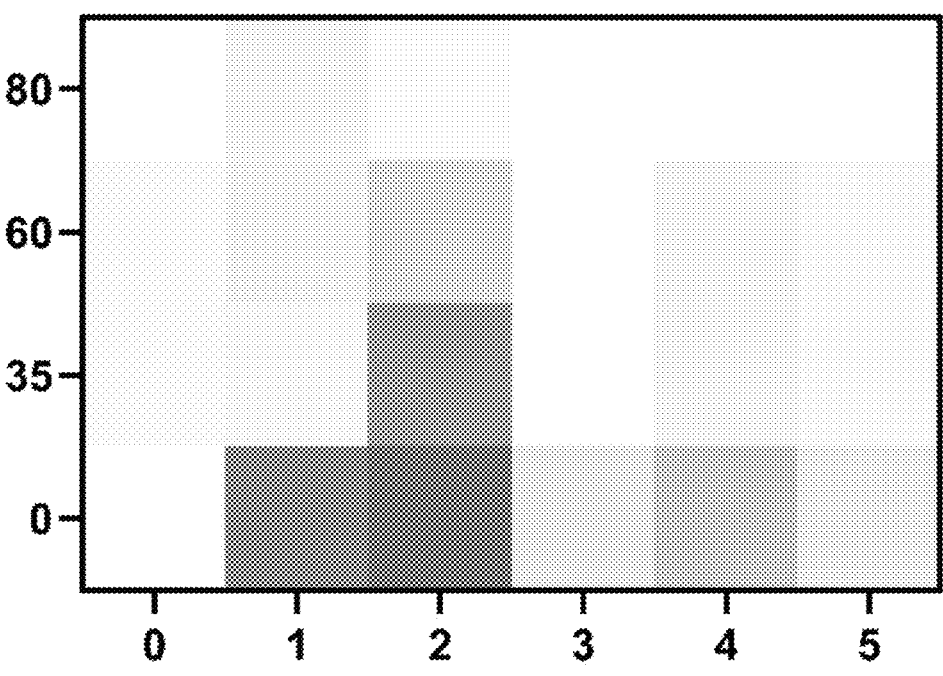
Figure 21:
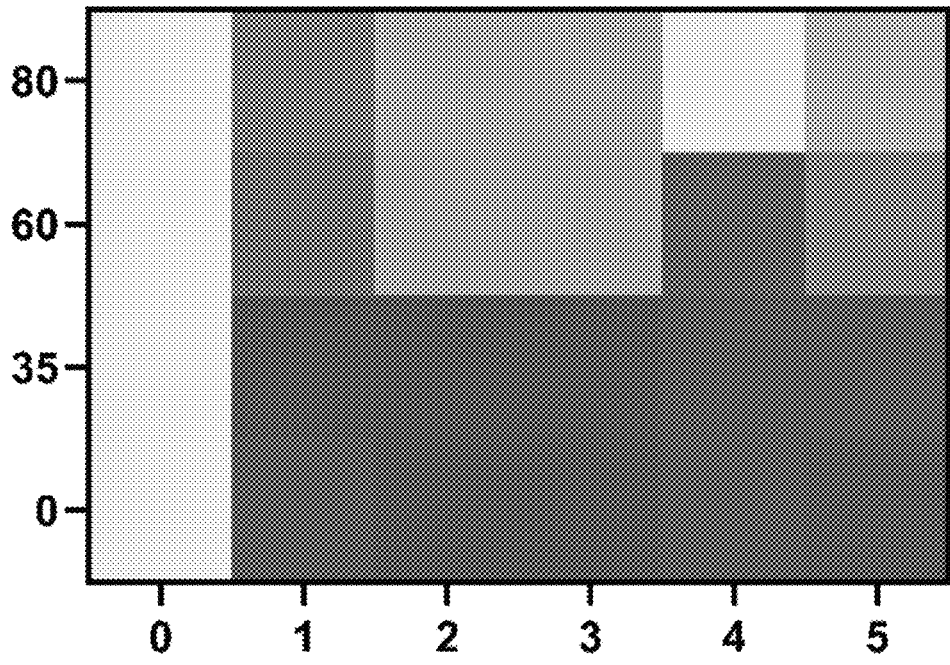

FIGS. 20 and 21 are heat maps showing the results of the same experiment using a strain of *P. putida* engineered to implement the genetic circuit shown in FIG. 6. FIG. 20 shows the results of the experiment in soil without fungus, and FIG. 21 shows the results of the experiment in soil with fungus.

Figure 22:
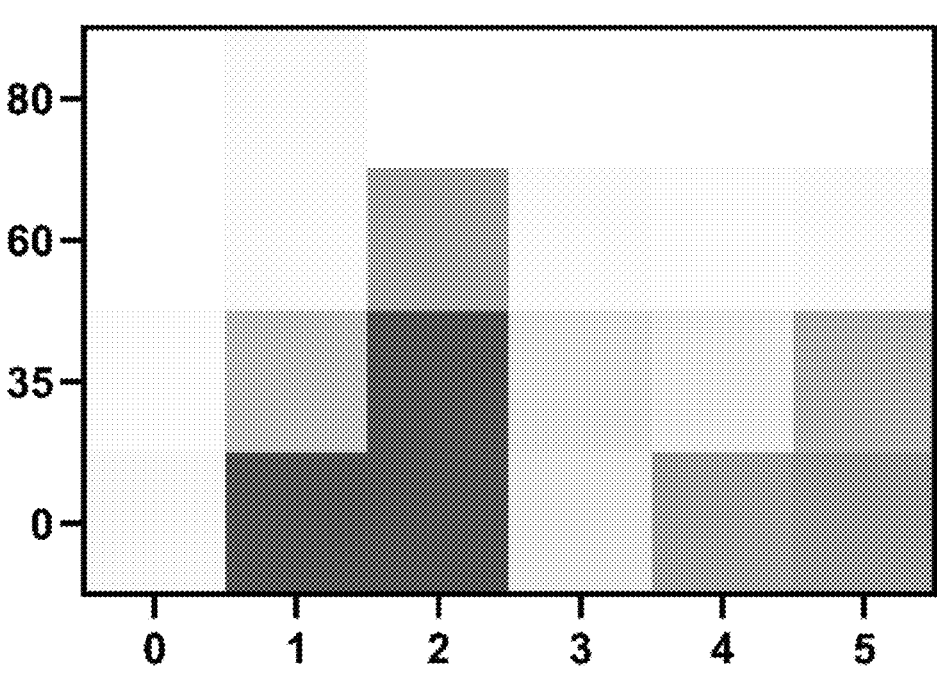
Figure 23:
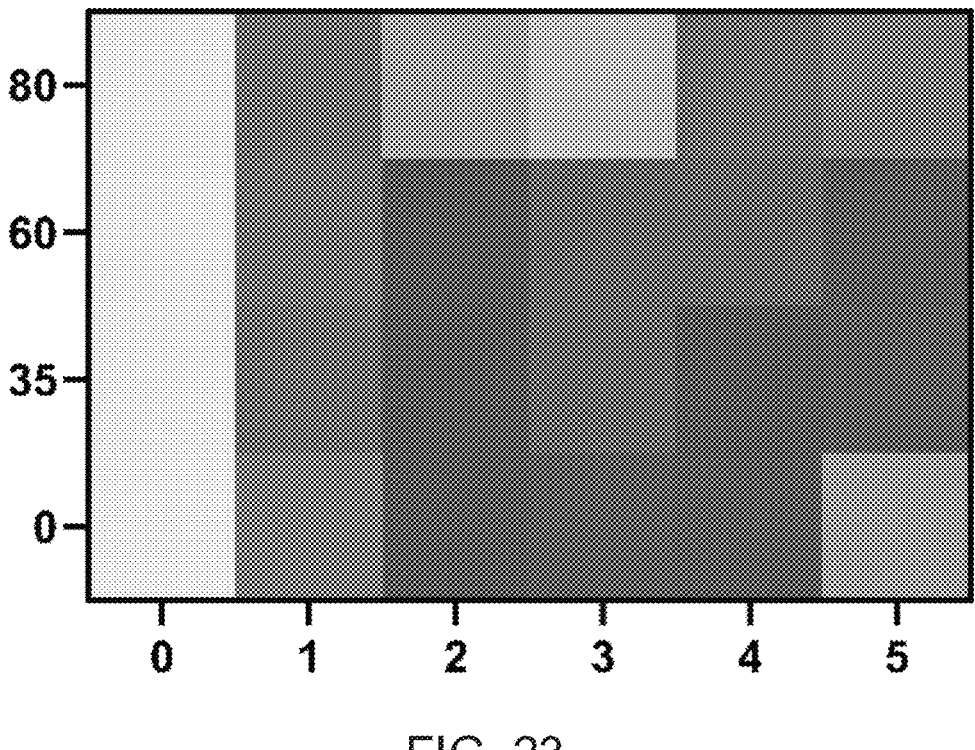

FIGS. 22 and 23 are heat maps showing the results of the same experiment using the same strain of *P. putida*, but with 3O-C6-HSL as the input as shown in the genetic circuit of FIG. 7. FIG. 22 shows the results of the experiment in soil without fungus, and FIG. 23 shows the results of the experiment in soil with fungus.

Chemo-Attraction in Soil

Figure 24:
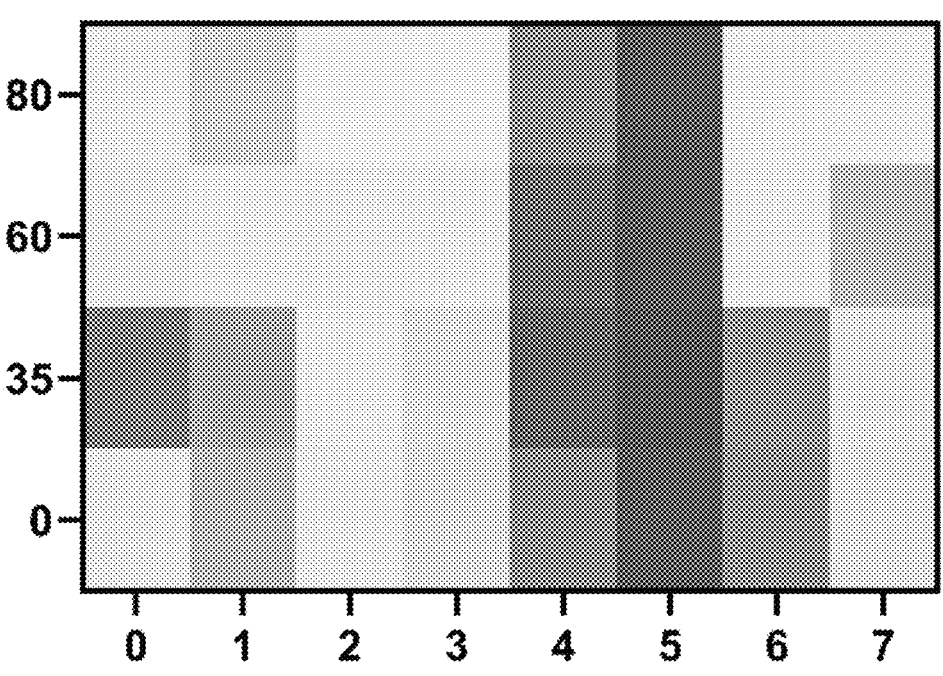
FIGS. 24-27 are heat maps of fluorescence of bacteria at different heights in a soil column over multiple days with and without a chemoattractant.
Figure 25:
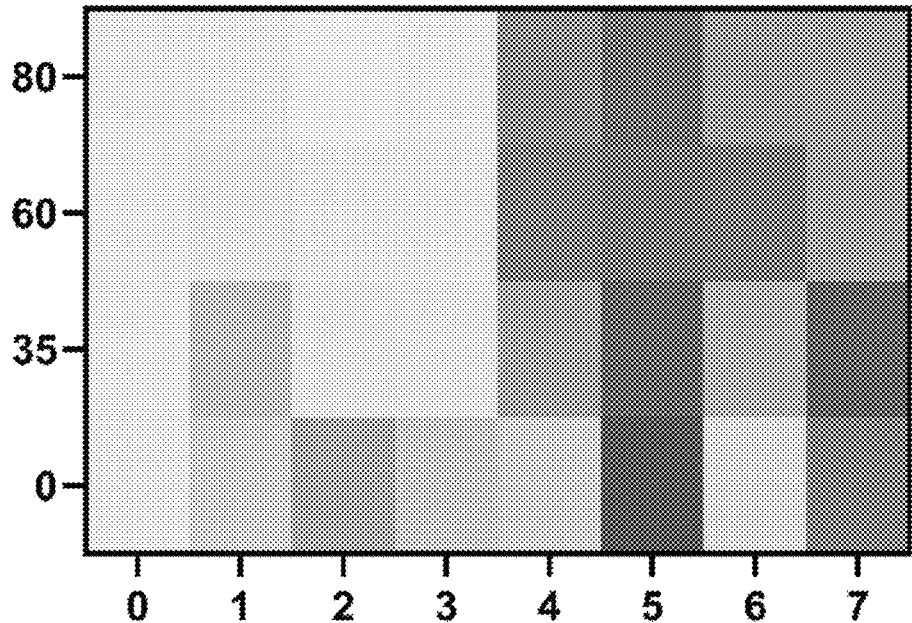
Figure 26:
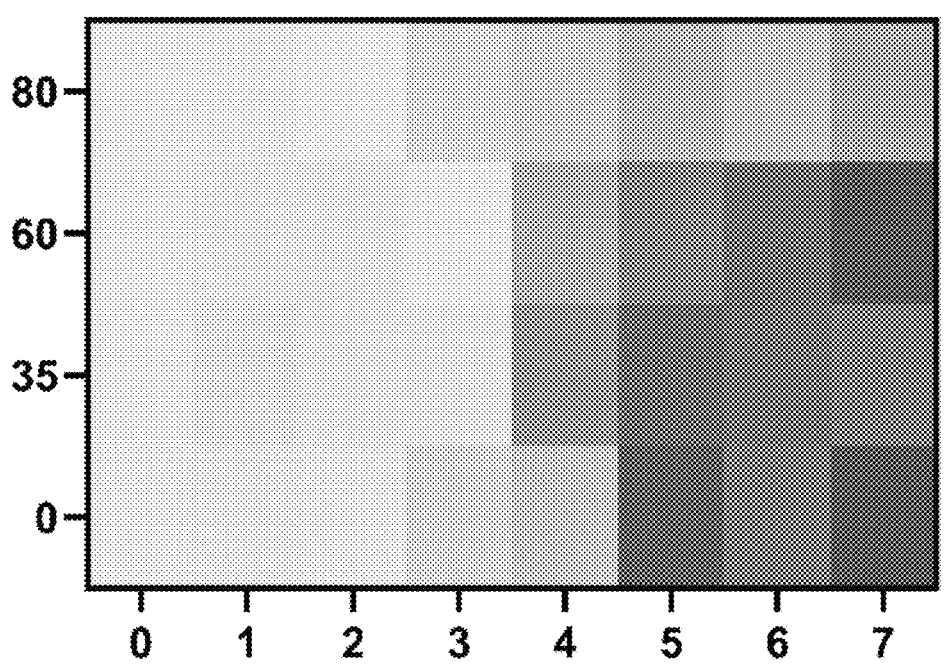
Figure 27:
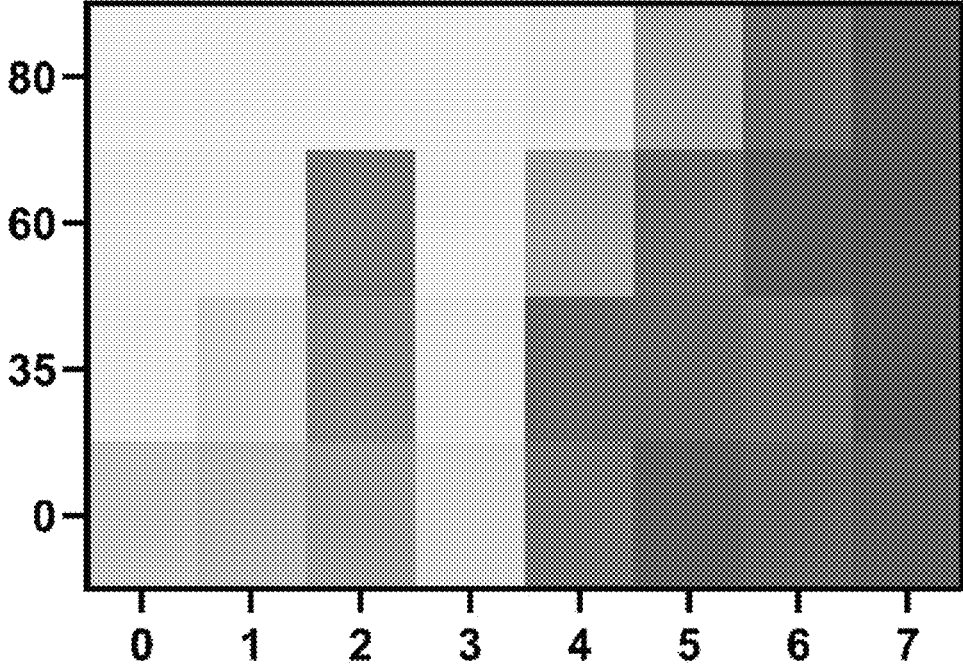

To enhance propagation of the signal in the soil column, salicylic acid was used as a chemoattractant molecule. Different concentrations of salicylic acid including 0.25, 1 and 2 mg/ml was tested on soil column to enhanced bacterial migration to the top of soil column from bottom. To test the migration rate of bacteria soil column was prepared with and without fungus. *P. putida* ($OD_{600}$ 5) having RFP integration, was inoculated at the bottom of soil column. Followed by 500 µl of salicylic acid with different concentration was added on the top of soil column. Migration of *P. putida* was tracked by collecting the soil. FIG. 24 is a heat map showing the fluorescence at different depths over 7 days when water is used as a control instead of salicylic acid. FIG. 25 is a heat map of the experiment when salicylic acid is used as a chemoattractant. Both FIGS. 24 and 25 show the results of the experiment performed in soil without fungus. FIG. 26 shows the results of experiment performed with water in soil with fungus, and FIG. 27 shows the results of the experiment performed with salicylic acid in soil with fungus.

Sampling and Analysis of the Soil in Flow Cytometer

To prepare the samples, resuspended soil was centrifuged at 1000×g for 10 min followed by supernatant was collected. Further 5 µl supernatant was added in the well already filled with 195 µl water Samples were run in a 96 well plate using cytoflex S (Beckman coulter, Unites states). The gain value to run the sample were FSC-500; SSC-1000; Violet SSC-50; GFP-90 and RFP-100 as acquisition setting. Flow rate to run the samples was maintained to 10 µl/min and 50000 events have been recorded. The data generated using the flow cytometer was further analyzed using FlowJo and TASBE software.

ADDITIONAL EXAMPLES

The following enumerated examples describe additional methods of detecting target analytes in subsurface soil and surface-dispersible microbial sensors for detecting a target analyte in subsurface soil.

Example 1. A method of detecting a target analyte in subsurface soil, comprising:

providing a sensor bacterium, a signal propagation bacterium, and a display bacterium at a soil surface;

allowing the sensor bacterium and the signal propagation bacterium to migrate into subsurface soil below the soil surface; and observing an output from the display bacterium when the sensor bacterium is exposed to the target analyte in the subsurface soil and produces a signal molecule in response to the presence of the target analyte, and the signal propagation bacterium amplifies the signal molecule by producing additional signal molecules in response to the presence of the signal molecule, and the display bacterium produces an observable signal in response to presence of the signal molecule.

Example 2. The method of example 1, wherein the sensor bacterium and the signal propagation bacterium are a single bacterial strain that produces the signal molecule in response to the presence of the target analyte and produces additional signal molecules in response to the presence of the signal molecule.

Example 3. The method of example 2, wherein the sensor bacterium, the signal propagation bacterium, and the display bacterium are all the single bacterial strain, wherein the bacterial strain also produces the observable signal in response to presence of the signal molecule.

Example 4. The method of any of examples 1 to 3, wherein the signal molecule is the target analyte.

Example 5. The method of any of examples 1 to 4, wherein the sensor bacterium, signal propagation bacterium, display bacterium, or a combination thereof implement a quorum sensing genetic circuit.

Example 6. The method of example 5, wherein the quorum sensing genetic circuit utilizes a homoserine lactone as a quorum sensing molecule.

Example 7. The method of example 6, wherein the sensor bacterium, signal propagation bacterium, display bacterium, or a combination thereof is an engineered bacterium to which the quorum sensing genetic circuit has been introduced by genetic modification.

Example 8. The method of any of examples 1 to 7, further comprising providing a fungus having filaments in the subsurface soil, wherein the fungus facilitates the migration of the sensor bacterium into the subsurface soil, or the migration of the signal propagation bacterium into the subsurface soil, or transfer of signal molecules between the bacteria, or a combination thereof.

Example 9. The method of example 8, wherein the fungus comprises *Lyophylum atratum, Rhizopus oryzae, Fusarium* sp., *Fusarium oxysporum, Fusarium chlamydosporum, Fusarium equiseti, Fusarium nygamai, Chaetomium* sp., *Chaetomium globosum, Morchella crassipes, Trichoderma* sp., or a combination thereof.

Example 10. The method of example 8, wherein fungus exchanges nutrients with the sensor bacterium, the signal propagation bacterium, the display bacterium, or a combination thereof.

Example 11. The method of example 8, wherein the sensor bacterium, the signal-propagation bacterium, the display bacterium, or a combination thereof, form a biofilm on a surface of the fungus.

Example 12. The method of example 8, wherein the fungus grows filaments in the subsurface soil at a growth rate from about 0.5 mm/day to about 10 mm/day.

Example 13. The method of any of examples 1 to 12, wherein the sensor bacterium, the signal propagation bacterium, the display bacterium, or a combination thereof comprise a strain of: *Pseudomonas putida, Pseudomonas frederiksbergensis, Escherichia coli, Variovorax soli, Olivibacter soli, Acinetobacter calcoaceticus, Stenotrophomonas maltophilia, Stemotrophomonas rhizophila, Stenotrophomonas humi, Achromobacter spanius, Achromobacter mucicolens, Ochrobactrum* sp., *Ochrobactrum pecoris,* or a combination thereof.

Example 14. The method of any of examples 1 to 13, wherein the target analyte is a quorum sensing molecule, a homoserine lactone, an explosive compound, trinitrotoluene, dinitrotoluene, a pollutant, a pharmaceutical, a nutrient, a sugar, or a combination thereof.

Example 15. The method of any of examples 1 to 14, wherein providing the sensor bacterium, signal propagation bacterium, and display bacterium at the soil surface comprises spreading the bacteria on the undisturbed soil surface, or mixing the bacteria into surface soil, or inserting plugs containing the bacteria into the soil.

Example 16. A surface-dispersible microbial sensor for detecting a target analyte in subsurface soil, comprising:

a sensor bacterium that produces a signal molecule in response to presence of a target analyte, wherein the sensor bacterium is capable of migrating into subsurface soil from a soil surface;

a signal propagation bacterium that amplifies the signal molecule by producing additional signal molecules in response to the presence of the signal molecule, wherein the signal propagation bacterium is capable of migrating into subsurface soil from the soil surface; and a display bacterium that produces an observable signal in response to presence of the signal molecule.

Example 17. The microbial sensor of example 16, wherein the sensor bacterium and the signal propagation bacterium are a single bacterial strain that produces the signal molecule in response to the presence of the target analyte and produces additional signal molecules in response to the presence of the signal molecule.

Example 18. The microbial sensor of example 17, wherein the sensor bacterium, the signal propagation bacterium, and the display bacterium are all the single bacterial strain, wherein the bacterial strain also produces the observable signal in response to presence of the signal molecule.

Example 19. The microbial sensor of claim 16, wherein the signal molecule is the target analyte.

Example 20. The microbial sensor of any of examples 16 to 19, wherein the sensor bacterium, signal propagation bacterium, display bacterium, or a combination thereof implement a quorum sensing genetic circuit.

Example 21. The microbial sensor of any of example 20, wherein the quorum sensing genetic circuit utilizes a homoserine lactone as a quorum sensing molecule.

Example 22. The microbial sensor of example 21, wherein the sensor bacterium, signal propagation bacterium, display bacterium, or a combination thereof is an engineered bacterium to which the quorum sensing genetic circuit has been introduced by genetic modification.

Example 23. The microbial sensor of any of examples 16 to 22, further comprising a fungus that facilitates the migration of the sensor bacterium into the subsurface soil, or the migration of the signal propagation bacterium into the subsurface soil, or transfer of signal molecules between the bacteria, or a combination thereof.

Example 24. The microbial sensor of example 23, wherein the fungus comprises *Lyophylum atratum, Rhizopus oryzae, Fusarium* sp., *Fusarium oxysporum, Fusarium chlamydosporum, Fusarium equiseti, Fusarium* nygamai,

*Chaetomium* sp., *Chaetomium globosum, Morchella crassipes, Trichoderma* sp., or a combination thereof.

Example 25. The microbial sensor of example 23, wherein fungus exchanges nutrients with the sensor bacterium, the signal propagation bacterium, the display bacterium, or a combination thereof.

Example 26. The microbial sensor of example 23, wherein the sensor bacterium, the signal-propagation bacterium, the display bacterium, or a combination thereof, form a biofilm on a surface of the fungus.

Example 27. The microbial sensor of example 23, wherein the fungus grows filaments in subsurface soil at a growth rate from about 0.5 mm/day to about 10 mm/day.

Example 28. The microbial sensor of any of examples 16 to 27, wherein the sensor bacterium, the signal propagation bacterium, the display bacterium, or a combination thereof comprise a strain of: *Pseudomonas putida, Pseudomonas frederiksbergensis, Escherichia coli, Variovorax soli, Olivibacter soli, Acinetobacter calcoaceticus, Stenotrophomonas maltophilia, Stemotrophomonas rhizophila, Stenotrophomonas humi, Achromobacter spanius, Achromobacter mucicolens, Ochrobactrum* sp., *Ochrobactrum pecoris*, or a combination thereof.

Example 29. The microbial sensor of any of examples 16 to 28, wherein the target analyte is a quorum sensing molecule, a homoserine lactone, an explosive compound, trinitrotoluene, dinitrotoluene, a pollutant, a pharmaceutical, a nutrient, a sugar or a combination thereof.

Example 30. A microbial sensor as recited herein, wherein the at least one of the organisms (i.e. bacterium) includes one or more sequence from SEQ ID NOS: 1-7, or a combination thereof.

Example 31. A microbial sensor as recited in example 30, wherein the one or more sequences is at least 80%, at least 85%, at least 90%, or at least 95% homologous to one or more of SEQ ID NOS: 1-7.

Example 32. A microbial sensor as recited in either example 30 or 31, wherein the bacterium includes *p. putida*.

Example 33. A microbial sensor as recited in example 32, wherein each of display bacterium, the signal bacterium, and the sensor bacterium each comprise *p. putida*.

Example 34. A genetic circuit for use in a microbial sensor comprising one or more sequences selected from SEQ ID NOS: 1-7.

Example 35. A genetic circuit as recited in example 34 wherein the one or more sequences is at least 80%, at least 85%, at least 90%, or at least 95% homologous to one or more of SEQ ID NOS: 1-7.

Example 36. A genetic circuit as recited in either of examples 34 or 35 contained in one or more bacterium.

Example 37. A genetic circuit as recited in any of examples 34-36, wherein the circuit is keyed to detect a target analyte.

Example 38. A genetic circuit as recited in example 37, wherein the target analyte is an analyte recited herein.

It is to be understood that the examples of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular examples only and is not intended to be limiting.

Reference throughout this specification to "one example" or "an example" means that a particular feature, structure, or characteristic described in connection with the example is included in at least one example of the present invention. Thus, appearances of the phrases "in one example" or "in an example" in various places throughout this specification are not necessarily all referring to the same example.

Although the disclosure may not expressly disclose that some examples or features described herein may be combined or interchanged with other examples or features described herein, this disclosure should be read to describe any such combinations that would be practicable by one of ordinary skill in the art no matter the specific examples that were described. Indeed, unless a certain combination of elements or functions not expressly disclosed would conflict with one another, such that the combination would render the resulting example inoperable or impracticable as would be apparent to those skilled in the art, this disclosure is meant to contemplate that any disclosed element or feature or function in any example described herein can be incorporated into any other example described herein (e.g., the elements or features or functions combined or interchanged with other elements or features or functions across examples) even though such combinations or interchange of elements or features or functions and resulting examples may not have been specifically or expressly disclosed and described. The use of "or" in this disclosure should be understood to mean non-exclusive or, i.e., "and/or," unless otherwise indicated herein.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various examples of the present invention can be referred to herein along with alternatives for the various components thereof. It is understood that such examples and alternatives are not to be construed as de facto equivalents of one another, but are to be considered as separate and autonomous representations of the present invention.

Furthermore, the described features, structures, or characteristics can be combined in any suitable manner in one or more examples. In the description, numerous specific details are provided, such as examples of lengths, widths, shapes, etc., to provide a thorough understanding of examples of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

What is claimed is:

1. A method of detecting a target analyte in subsurface soil, comprising:

providing a sensor bacterium, a signal propagation bacterium, and a display bacterium at a soil surface;

allowing the sensor bacterium and the signal propagation bacterium to migrate into subsurface soil below the soil surface; and observing an output from the display bacterium when the sensor bacterium is exposed to the target analyte in the subsurface soil and produces a signal molecule in response to the presence of the target analyte, and the signal propagation bacterium amplifies the signal molecule by producing additional signal molecules in response to the presence of the signal molecule, and the display bacterium produces an observable signal in response to presence of the signal molecule.

2. The method of claim 1, wherein the sensor bacterium and the signal propagation bacterium are a single bacterial strain that produces the signal molecule in response to the presence of the target analyte and produces additional signal molecules in response to the presence of the signal molecule.

3. The method of claim 2, wherein the sensor bacterium, the signal propagation bacterium, and the display bacterium are all the single bacterial strain, wherein the bacterial strain also produces the observable signal in response to presence of the signal molecule.

4. The method of claim 1, wherein the signal molecule is the target analyte.

5. The method of claim 1, wherein the sensor bacterium, signal propagation bacterium, display bacterium, or a combination thereof implement a quorum sensing genetic circuit.

6. The method of claim 5, wherein the quorum sensing genetic circuit utilizes a homoserine lactone as a quorum sensing molecule.

7. The method of claim 6, wherein the sensor bacterium, signal propagation bacterium, display bacterium, or a combination thereof is an engineered bacterium to which the quorum sensing genetic circuit has been introduced by genetic modification.

8. The method of claim 1, further comprising providing a fungus having filaments in the subsurface soil, wherein the fungus facilitates the migration of the sensor bacterium into the subsurface soil, or the migration of the signal propagation bacterium into the subsurface soil, or transfer of signal molecules between the bacteria, or a combination thereof.

9. The method of claim 8, wherein the fungus comprises *Lyophylum atratum, Rhizopus oryzae, Fusarium* sp., *Fusarium oxysporum, Fusarium chlamydosporum, Fusarium equiseti, Fusarium nygamai, Chaetomium* sp., *Chaetomium globosum, Morchella crassipes, Trichoderma* sp., or a combination thereof.

10. The method of claim 8, wherein fungus exchanges nutrients with the sensor bacterium, the signal propagation bacterium, the display bacterium, or a combination thereof.

11. The method of claim 8, wherein the sensor bacterium, the signal-propagation bacterium, the display bacterium, or a combination thereof, form a biofilm on a surface of the fungus.

12. The method of claim 8, wherein the fungus grows filaments in the subsurface soil at a growth rate from about 0.5 mm/day to about 10 mm/day.

13. The method of claim 1, wherein the sensor bacterium, the signal propagation bacterium, the display bacterium, or a combination thereof comprise a strain of: *Pseudomonas putida, Pseudomonas frederiksbergensis, Escherichia coli, Variovorax soli, Olivibacter soli, Acinetobacter calcoaceticus, Stenotrophomonas maltophilia, Stemotrophomonas rhizophila, Stenotrophomonas humi, Achromobacter spanius, Achromobacter mucicolens, Ochrobactrum* sp., *Ochrobactrum pecoris,* or a combination thereof.

14. The method of claim 1, wherein the target analyte is a quorum sensing molecule, a homoserine lactone, an explosive compound, trinitrotoluene, dinitrotoluene, a pollutant, a pharmaceutical, a nutrient, a sugar or a combination thereof.

15. The method of claim 1, wherein providing the sensor bacterium, signal propagation bacterium, and display bacterium at the soil surface comprises spreading the bacteria on the undisturbed soil surface, or mixing the bacteria into surface soil, or inserting plugs containing the bacteria into the soil.

16. A surface-dispersible microbial sensor for detecting a target analyte in subsurface soil, comprising: a sensor bacterium configured to produce a signal molecule in response to presence of a target analyte, wherein the sensor bacterium is configured to migrate into subsurface soil from a soil surface; a signal propagation bacterium configured to amplify the signal molecule by producing additional signal molecules in response to the presence of the signal molecule, wherein the signal propagation bacterium is capable of migrating into subsurface soil from the soil surface; and a display bacterium configured to produce an observable signal in response to presence of the signal molecule.

17. The microbial sensor of claim 16, wherein the sensor bacterium and the signal propagation bacterium are a single bacterial strain configured to produce the signal molecule in response to the presence of the target analyte and produces additional signal molecules in response to the presence of the signal molecule.

18. The microbial sensor of claim 17, wherein the sensor bacterium, the signal propagation bacterium, and the display bacterium are all the single bacterial strain, wherein the bacterial strain also produces the observable signal in response to presence of the signal molecule.

19. The microbial sensor of claim 16, wherein the signal molecule is the target analyte.

20. The microbial sensor of claim 16, wherein the sensor bacterium, signal propagation bacterium, display bacterium, or a combination thereof implement a quorum sensing genetic circuit.

21. The microbial sensor of claim 20, wherein the quorum sensing genetic circuit is configured to utilize a homoserine lactone as a quorum sensing molecule.

22. The microbial sensor of claim 21, wherein the sensor bacterium, signal propagation bacterium, display bacterium, or a combination thereof is an engineered bacterium to which the quorum sensing genetic circuit has been introduced by genetic modification.

23. The microbial sensor of claim 16, further comprising a fungus configured to facilitate the migration of the sensor bacterium into the subsurface soil, or the migration of the signal propagation bacterium into the subsurface soil, or transfer of signal molecules between the bacteria, or a combination thereof.

24. The microbial sensor of claim 23, wherein the fungus comprises *Lyophylum atratum, Rhizopus oryzae, Fusarium* sp., *Fusarium oxysporum, Fusarium chlamydosporum, Fusarium equiseti, Fusarium nygamai, Chaetomium* sp., *Chaetomium globosum, Morchella crassipes, Trichoderma* sp., or a combination thereof.

25. The microbial sensor of claim 23, wherein fungus exchanges nutrients with the sensor bacterium, the signal propagation bacterium, the display bacterium, or a combination thereof.

26. The microbial sensor of claim 23, wherein the sensor bacterium, the signal-propagation bacterium, the display bacterium, or a combination thereof, form a biofilm on a surface of the fungus.

27. The microbial sensor of claim 23, wherein the fungus grows filaments in subsurface soil at a growth rate from about 0.5 mm/day to about 10 mm/day.

28. The microbial sensor of claim 16, wherein the sensor bacterium, the signal propagation bacterium, the display bacterium, or a combination thereof comprise a strain of: *Pseudomonas putida, Pseudomonas frederiksbergensis, Escherichia coli, Variovorax soli, Olivibacter soli, Acinetobacter calcoaceticus, Stenotrophomonas maltophilia, Stemotrophomonas rhizophila, Stenotrophomonas humi, Achromobacter spanius, Achromobacter mucicolens, Ochrobactrum* sp., *Ochrobactrum pecoris*, or a combination thereof.

29. The microbial sensor of claim 16, wherein the target analyte is a quorum sensing molecule, a homoserine lactone, an explosive compound, trinitrotoluene, dinitrotoluene, a pollutant, a pharmaceutical, a nutrient, a sugar, or a combination thereof.

\*  \*  \*  \*  \*

SEQUENCE LISTING

```
Sequence total quantity: 7
SEQ ID NO: 1              moltype = DNA  length = 822
FEATURE                   Location/Qualifiers
source                    1..822
                          mol_type = unassigned DNA
                          organism = Synthetic construct
SEQUENCE: 1
gatccgagct gttgacaatt aatcatcggc tcgtataatg tgtggaattg tgagcggata   60
acaatttcac acaggaaaca gaatcatatg gtcagcaaag gcgaagaaga caacatggct  120
tccctcccgg ctacgcacga actgcacatc tttggcagca tcaatggcgt ggactttgac  180
atggtcggtc aaggcaccgg taacccgaac gacggctacg aggagctgaa cctgaagagc  240
acgaaggggg acctccagtt cagcccttgg attctggtgc cccacattgg ttacggtttc  300
catcagtacc tgccgtaccc ggacggcatg tccccattcc aggccgcaat ggtggatggc  360
agcggctacc aagttcaccg taccatgcag tttgaggacg gggcgagttt gaccgttaat  420
taccgctaca cctatgaggg ctcccatatc aagggtgaag cccaagtaaa gggcaccggc  480
tttcctgcgg acgggcccgt gatgaccaac tcgctgaccg cggccgattg gtgtcgttcc  540
aaaaagacgt atccgaacga caagaccatc atcagtacct ttaagtggag ctacaccacc  600
gggaacggca agcgctatcg ttcgacggcg cgcacgacct acacgttcgc taagccgatg  660
gccgccaact atctcaagaa ccagccaatg tacgtgttcc gcaaaaccga gttgaagcac  720
tcgaagaccg aactgaactt caaggaatgg cagaaggcgt tcacggacgt gatgggcatg  780
gacgagctgt ataaggacta caaggacgat gacgacaagt aa                    822

SEQ ID NO: 2              moltype = DNA  length = 707
FEATURE                   Location/Qualifiers
source                    1..707
                          mol_type = unassigned DNA
                          organism = Synthetic construct
SEQUENCE: 2
atccttcgag cctagcaagg gtccgggttc accgaaatct atctcatttg ctagttataa   60
aattatgaaa tttgcgtaaa ttcttcagaa agaatcctat cccaataagg aggtatatta  120
atgactataa tgataaaaaa atcggatttt ttggcaattc catcggagga gtataaaggt  180
attctaagtc tccgttatca agtgtttaag caaagacttg agtgggactt agttgtagaa  240
aataaccttg aatcagatga gtatgataac tcaaatgcag aatatattta tgcttgtgat  300
gatactgaaa atgtaagtgg atgctggcgt ttattaccta caacaggtga ttatatgctg  360
aaaagtgttt ttcctgaatt gcttggtcaa cagagtgctc ccaaagatcc taatatagtc  420
gaattaagtc gttttgctgt aggtaaaaat agctcaaaga taaataactc tgctagtgaa  480
attacaatga aactatttga agctatatat aaacacgctg ttagtcaagg tattacagaa  540
tatgtaacag taacatcaac agcaatagag cgatttttaa agcgtattaa agttccttgt  600
catcgtattg gagacaaaga aattcatgta ttaggtgata ctaaatcggt tgtattgtct  660
atgcctatta atgaacagtt taaaaaagca gtcttaaatt aatctgg              707

SEQ ID NO: 3              moltype = DNA  length = 888
FEATURE                   Location/Qualifiers
source                    1..888
                          mol_type = unassigned DNA
                          organism = Synthetic construct
SEQUENCE: 3
atccactatt gtatcgctgg gaatacaatt acttaacata agcacctgta ggatcgtaca   60
ggtttacgca agaaaatggt ttgttatagt cgaatatgaa agaatcctat cccaataagg  120
aggtatatta atgaaaaaca taaatgccga cgacacatac agaataatta ataaaattaa  180
agcttgtaga agcaataatg atattaatca atgcttatct gatatgacta aaatggtaca  240
ttgtgaatat tatttactcg cgatcattta tcctcattct atggttaaat ctgatatttc  300
aattctagat aattacccta aaaaatggag gcaatattat gatgacgcta atttaataaa  360
atatgatcct atagtagatt attctaactc caatcattca ccaattaatt ggaatatatt  420
tgaaaacaat gctgtaaata aaaaatctcc aaatgtaatt aaagaagcga aaacatcagg  480
tcttatcact gggtttagtt tccctattca tacggctaac aatggcttcg gaatgcttag  540
ttttgcacat tcagaaaaag acaactatat agatagttta tttttacatg cgtgtatgaa  600
cataccatta attgttcctt ctctagttga taattatcga aaaataaata tagcaaataa  660
taaatcaaac aacgatttaa ccaaaagaga aaaagaatgt ttagcgtggg catgcgaagg  720
aaaaagctct tgggatattt caaaaatatt aggctgcagt gagcgtactg tcactttcca  780
tttaaccaat gcgcaaatga aactcaatac aacaaaccgc tgccaaagta tttctaaagc  840
```

-continued

```
aattttaaca ggagcaattg attgcccata ctttaaaaat taagctgg              888

SEQ ID NO: 4          moltype = DNA   length = 734
FEATURE               Location/Qualifiers
source                1..734
                      mol_type = unassigned DNA
                      organism = Synthetic construct
SEQUENCE: 4
atccttcgag cctagcaagg gtccgggttc accgaaatct atctcatttg ctagttataa  60
aattatgaaa tttgcgtaaa ttcttcagaa agaatcctat cccaataagg aggtatatta  120
atgattgttc agattggccg tcgtgaggaa tttgataaaa agctgctggg cgagatgcac  180
aaaactgcgtg cacaggtttt caaggagcgt aaaggttggg acgttagcgt tattgacgaa  240
atggagattg atggctacga cgctctgtct ccgtattata tgctgattca ggaggacacc  300
ccggaagctc aggtatttgg ttgctggcgt atcttcgata ctacgggtcc gtatatgctg  360
aaaaatacct tcccggaact gctgcacggt aaagaagcgc cttgtagccc gcacatctgg  420
gaactgtctc gtttcgctat caactccggc cagaaaggtt ccctgggctt ttccgattgt  480
accctggaag caatgcgtgc gctggcgcgc tattcactgc aaaacgacat ccagactctg  540
gtgaccgtta ctactgtggg cgttgaaaag atgatgatcc gtgcaggcct ggacgttagc  600
cgtttcggtc cacacctgaa gatcggtatc gaacgcgcgg tggccctgcg tatcgaactg  660
aatgcaaaaa cccagatcgc actgtatggt ggtgttctgg tggaacaacg cctggccgtt  720
tcctaataat ctgg                                                   734

SEQ ID NO: 5          moltype = DNA   length = 745
FEATURE               Location/Qualifiers
source                1..745
                      mol_type = unassigned DNA
                      organism = Synthetic construct
SEQUENCE: 5
atccactatt gtatcgctgg gaatacaatt acttaacata agcacctgta ggatcgtaca  60
ggtttacgca agaaaatggt ttgttatagt cgaatatgaa agaatcctat cccaataagg  120
aggtatatta atgattgttc agattggccg tcgtgaggaa tttgataaaa agctgctggg  180
cgagatgcac aaaactgcgtg cacaggtttt caaggagcgt aaaggttggg acgttagcgt  240
tattgacgaa atggagattg atggctacga cgctctgtct ccgtattata tgctgattca  300
ggaggacacc ccggaagctc aggtatttgg ttgctggcgt atcttcgata ctacgggtcc  360
gtatatgctg aaaaatacct tcccggaact gctgcacggt aaagaagcgc cttgtagccc  420
gcacatctgg gaactgtctc gtttcgctat caactccggc cagaaaggtt ccctgggctt  480
ttccgattgt accctggaag caatgcgtgc gctggcgcgc tattcactgc aaaacgacat  540
ccagactctg gtgaccgtta ctactgtggg cgttgaaaag atgatgatcc gtgcaggcct  600
ggacgttagc cgtttcggtc cacacctgaa gatcggtatc gaacgcgcgg tggccctgcg  660
tatcgaactg aatgcaaaaa cccagatcgc actgtatggt ggtgttctgg tggaacaacg  720
cctggccgtt tcctaataag ctggt                                       745

SEQ ID NO: 6          moltype = DNA   length = 1584
FEATURE               Location/Qualifiers
source                1..1584
                      mol_type = other DNA
                      organism = Synthetic construct
SEQUENCE: 6
atccactatt gtatcgctgg gaatacaatt acttaacata agcacctgta ggatcgtaca  60
ggtttacgca agaaaatggt ttgttatagt cgaatattat aataagtaat tcttaagggg  120
gtaagtccaa tggtatccaa gggcgaagag gtgatcaagg aatttatgcg cttcaaggtg  180
cgcatggaag gctccatgaa cggccatgaa ttcgagattg aaggcgaagg tgaaggccgc  240
ccctacgaag gtacccagac ggccaagttg aaggtcacca agggtggccc tctgcctttc  300
gcgtgggaca tcctgagccc acagttcatg tatgggagca aggcttacgt taaacacccg  360
gccgatatcc cggactataa gaagctcagt tttcctgaag ggttcaagtg ggaacgcgtg  420
atgaatttcg aggatggtgg cctcgtaacc gtcacccaag acagcagcct gcaggatggc  480
accctgatct acaaggtaaa aatgcgcggc acgaacttcc ctccagatgg tccggttatg  540
caaaaaaaga ccatgggctg ggaagcctcg accgagcgtc tgtaccctcg tgacggcgtg  600
ctcaagggcg aaatccatca agccctgaaa ctgaaggatg gcggccatta cctggtcgag  660
ttcaaaacca tctatatggc taaaaagcca gtacagctgc cggggtatta ctatgttgac  720
acgaaactcg atattacctc ccacaatgag gactacacca tcgtggaaca gtacgaacgc  780
agcgaaggcc gtcatcatct ctttctcggc catggtaccg gctcgacggg ttccggcagc  840
agcggcaccg ccagcagcga ggacaacaat atggctgtca tcaaagagtt catgcgtttc  900
aaagtgacca tggagggtag catgaatggg cacgaatttg aaatcgaagg cgaaggtgaa  960
ggccgtccgt atgagggcac gcagaccgca aaattgaagg tgacgaaggg tggccccttg  1020
ccatttgctt gggacatttt gagcccgcag ttcatgtacg gttccaaggc atacgtgaaa  1080
catccagctg acatccctga ttacaagaag ctgagtttcc cggagggttt aaatgggaa  1140
cgggttatga atttcgagga cggcggcctg gtaacggtac cccaggattc cagcctgcaa  1200
gacggcaccc tcatttacaa agtgaagatg cgtgggacca acttcccgcc ggatggccct  1260
gttatgcaga agaaaaccat gggctgggaa gcgtcgaccg agcgcctcta cccgcgcgac  1320
ggcgtactga aggggggagat ccaccaggcc ctgaagctga aggacggtgg tcattacctg  1380
gtggagttca gaccatttta tatggccaaa aagcctgttc agttgccggg ctactactac  1440
gtcgacacca agctcgacat caccagccac aacgaggact acaccattgt ggagcagtac  1500
gagcgcagcg aaggccggca ccacttgttc ttgtatggca tggacgaact gtacaaagac  1560
tacaaggacg acgatgacaa ataa                                         1584

SEQ ID NO: 7          moltype = DNA   length = 842
FEATURE               Location/Qualifiers
source                1..842
```

```
                    mol_type = other DNA
                    organism = Synthetic construct
SEQUENCE: 7
gagctgttga caattaatca tcggctcgta taatgtgtgg aattgtgagc ggataacaat  60
ttcacacagg aaacagaatc ataatgaaaa acataaatgc cgacgacaca tacagaataa  120
ttaataaaat taaagcttgt agaagcaata atgatattaa tcaatgctta tctgatatga  180
ctaaaatggt acattgtgaa tattatttac tcgcgatcat ttatcctcat tctatggtta  240
aatctgatat ttcaattcta gataattacc ctaaaaaatg gaggcaatat tatgatgacg  300
ctaatttaat aaaatatgat cctatagtag attattctaa ctccaatcat tcaccaatta  360
attggaatat atttgaaaac aatgctgtaa ataaaaaatc tccaaatgta attaaagaag  420
cgaaaacatc aggtcttatc actgggttta gtttccctat tcatacggct aacaatggct  480
tcggaatgct tagttttgca cattcagaaa aagacaacta tatagatagt ttatttttac  540
atgcgtgtat gaacatacca ttaattgttc cttctctagt tgataattat cgaaaaataa  600
atatagcaaa taataaatca aacaacgatt taaccaaaag agaaaaagaa tgtttagcgt  660
gggcatgcga aggaaaaagc tcttgggata tttcaaaaat attaggctgc agtgagcgta  720
ctgtcacttt ccatttaacc aatgcgcaaa tgaaactcaa tacaacaaac cgctgccaaa  780
gtatttctaa agcaattta acaggagcaa ttgattgccc atactttaaa aattaagctg  840
gt                                                                842
```